US012630875B2

(12) United States Patent
Williams et al.

(10) Patent No.: US 12,630,875 B2
(45) Date of Patent: May 19, 2026

(54) METHODS FOR RAPID DNA EXTRACTION FROM TISSUE AND LIBRARY PREPARATION FOR NANOPORE-BASED SEQUENCING

(71) Applicant: The Trustees of Columbia University in the City of New York, New York, NY (US)

(72) Inventors: Samuel Zev Williams, New York, NY (US); Shan Wei, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1257 days.

(21) Appl. No.: 17/468,065

(22) Filed: Sep. 7, 2021

(65) Prior Publication Data

US 2021/0403994 A1     Dec. 30, 2021

Related U.S. Application Data

(63) Continuation of application No. PCT/US2020/021395, filed on Mar. 6, 2020.

(60) Provisional application No. 62/959,527, filed on Jan. 10, 2020, provisional application No. 62/814,607, filed on Mar. 6, 2019.

(51) Int. Cl.
C12Q 1/6869     (2018.01)
C12Q 1/6806     (2018.01)

(52) U.S. Cl.
CPC ......... C12Q 1/6869 (2013.01); C12Q 1/6806 (2013.01)

(58) Field of Classification Search
None
See application file for complete search history.

(56) References Cited

U.S. PATENT DOCUMENTS

| | | | |
|---|---|---|---|
| 8,268,564 B2 | 9/2012 | Roth et al. | |
| 8,318,434 B2 | 11/2012 | Cuppens | |
| 8,771,950 B2 | 7/2014 | Church et al. | |
| 9,469,874 B2 | 10/2016 | Chen et al. | |
| 9,834,760 B2 | 12/2017 | Knudsen et al. | |
| 2007/0122391 A1 | 5/2007 | Harrington et al. | |
| 2009/0023180 A1 | 1/2009 | Dillon | |
| 2014/0235506 A1 | 8/2014 | Hindson et al. | |
| 2018/0087050 A1 | 3/2018 | Zheng et al. | |
| 2018/0305683 A1 | 10/2018 | Sampas | |
| 2019/0264201 A1* | 8/2019 | Pugh ................. | C12N 15/1093 |

FOREIGN PATENT DOCUMENTS

| | | | | |
|---|---|---|---|---|
| WO | 2016191618 | 12/2016 | | |
| WO | WO-2018218226 A1 * | 11/2018 | ......... | C12N 15/1065 |

OTHER PUBLICATIONS

Rapid Barcoding Sequencing (SQK-RBK004), Nanopore Protocol (Year: 2018).*
Rapid multiplex small DNA sequencing on the MinION nanopore sequencing platform, bioRxiv (Year: 2018).*
Rapid preimplantation genetic screening (PGS) using a handheld, nanopore-based, DNA sequencer, BioRxiv, 274563 (Year: 2018).*
Rapid Short-Read sequencing and aneuploidy detection using MinION Nanopore Technology, Genetics, 202, 37-44 (Year: 2016).*
Bhattacharjee et al., "Development of DNA Confirmatory and High-Risk Diagnostic Testing for Newborns Using Targeted Next-Generation DNA Sequencing", Genetics in Medicine, vol. 17 / Issue 5, pp. 337-347, May 2015.
Lanman et al., "Analytical and Clinical Validation of a Digital Sequencing Panel for Quantitative, Highly Accurate Evaluation of Cell-Free Circulating Tumor Dna", PLoS One, vol. 10 / Issue 10, e0140712., Oct. 2015.
Wei., "Rapid short-read sequencing and aneuploidy detection using MinION nanopore technology", Genetics, vol. 202 / Issue 1, pp. 37-44, Jan. 2016.
Bianchi and Porter. Feb. 27, 2014 DNA sequencing versus standard prenatal aneuploidy screening. N Engl J Med 370:799-808.
Carp, et al. Feb. 2006. Embryonic karyotype in recurrent miscarriage with parental karyotypic aberrations. Fertility and sterility 85:446-450.
Chiu, et al. Dec. 23, 2008 Noninvasive prenatal diagnosis of fetal chromosomal aneuploidy by massively parallel genomic sequencing of DNA in maternal plasma. Proc Natl Acad Sci U S A 105:20458-63.
Fragouli, et al. 2011 Cytogenetic analysis of human blastocysts with the use of FISH, CGH and aCGH: scientific data and technical evaluation. Human Reproduction 26:480-90. Submitted Sep. 28, 2010.
Kent, Jan. 25, 2002. "BLAT—the BLAST-like alignment tool." Genome Res 12(4): 656-664.
Levy and Wapner. Feb. 2018. Prenatal diagnosis by chromosomal microarray analysis. Fertility and sterility 109:201-212.
Marr, et al. Sep. 10, 2018. Gene silencing by RNA interference in the ectogarasitic mite, Psorogtes ovis. Vet Res 49:112.
Martin, Aug. 2, 2011 Cutadapt removes adapter sequences from high-throughput seguencing reads. EMBnetjournal. 17:10-.
Miller, et al. Jan. 22, 2003. Precise determination of mitochondrial DNA copy number in human skeletal and cardiac muscle by a PCR-based assay: lack of change of copy number with age. Nucleic acids research 31 :e61.
Norton, et al. Apr. 23, 2015 Cell-free DNA analysis for noninvasive examination of trisomy. N Engl J Med 2015;372:1589-97.
Pajnic. Jun. 2016. Extraction of DNA from Human Skeletal Material, p. 89-108. In W. Goodwin (Ed.), Forensic DNA Typing Protocols. Springer New York, New York, NY.
Picelli, et al. May 4, 2014 Tn5 transposase and tagmentation procedures for massively scaled sequencing projects. Genome Res. 24(12):2033-40.

(Continued)

*Primary Examiner* — Juliet C Switzer
*Assistant Examiner* — Brian Ellis Young
(74) *Attorney, Agent, or Firm* — LEASON ELLIS LLP

(57) ABSTRACT

The present disclosure relates to improved methods for preparing, sequencing and analyzing short DNA fragments using handheld, nanopore-based sequencing technology as well as improved methods for extracting DNA, in particular genomic DNA, for any downstream application.

7 Claims, 16 Drawing Sheets

Specification includes a Sequence Listing.

(56)          References Cited

OTHER PUBLICATIONS

Potapov and Ong, Sep. 30, 2016 Examining Sources of Error in PCR by Single-Molecule Sequencing. PlosOne 12(1):e)169774.

Sahoo, et al. Jan. 2017 Comprehensive genetic analysis of pregnancy loss by chromosomal microarrays: outcomes, benefits, and challenges. Genetics in medicine : official journal of the American College of Medical Genetics. 19(1):83-89.

Tomaso, et al. 2010. Comparison of commercial DNA preparation kits for the detection of Brucellae in tissue using quantitative real-time PCR. BMC Infect Dis 10:100. Received Jun. 19, 2009.

Wang and Kong 2019. "pblat: a multithread blat algorithm speeding up aligning seguences to genomes." BMC Bioinformatics 20(1): 28. Received Mar. 27, 2018.

Wei, et al. Oct. 2018a. Rapid preimplantation genetic screening using a handheld, nanogore-based DNA sequencer. Fertility and sterility 110:910-916 e912.

Wei, et al. Oct. 2018b Rapid preimplantation genetic screening (PGS) using a handheld, nanogore-based, DNA sequencer. bioRXiv 2018:274563-63.

Zhang, et al. Dec. 10, 2015. Germline Mutations in Predisposition Genes in Pediatric Cancer. N Engl J Med 373:2336-2346.

Extended European Search Report in EP Application No. 20765931.9-1118/3935164, mailed Jun. 1, 2023 (10 pages).

Wei et al. "Rapid Multiplex Small DNA Sequencing on the MinION Nanopore Sequencing Platform' Genes Genomes Genetics", May 2018, vol. 8, pp. 1649-1657; abstract; figure 1; p. 1649, second column, fourth paragraph—p. 1650, first column, first paragraph; p. 1652, second column, first paragraph; p. 1653, second column, second paragraph; p. 1655, second column, fourth paragraph), chorionic villus (p. 1655, second column, fourth paragraph; figure 2, figure 2 legend; Table 1. DOI: https://doi.org/10.1534/g3.118.200087.

New England BioLabs "Instruction Manual NEBNext UltraII End Repair/dA-Tailing Module"; Publication [online]. Mar. 2020 [retrieved Jun. 12, 2020]. Retrieved from the Internet: <URL:https://www.neb.com/-/media/nebus/files/manuals/manuale7546.pdf?rev-83f6dt6965564e1aaa43c955ede91f24&hash=D78A9D4E8F7E19E1EAAA8116DDCCF1EA>; pp. 1-3; p. 2, 1.4.

* cited by examiner

Figure 2
Figure 2A
Figure 2B
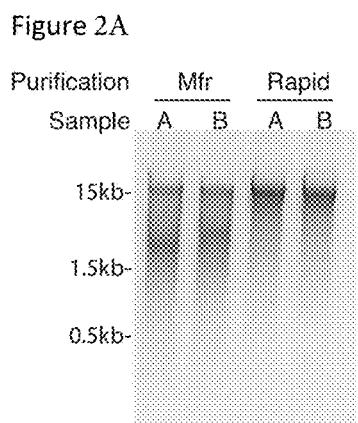
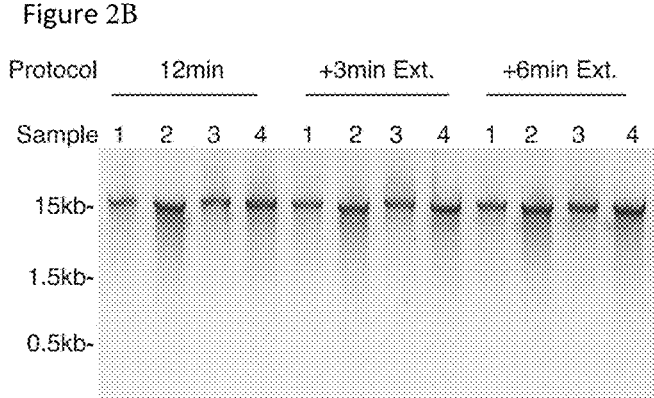
Figure 2C
Figure 2D
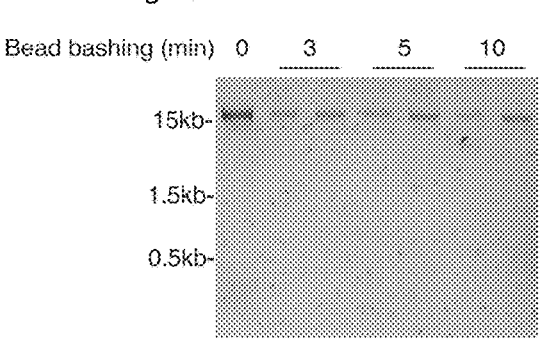
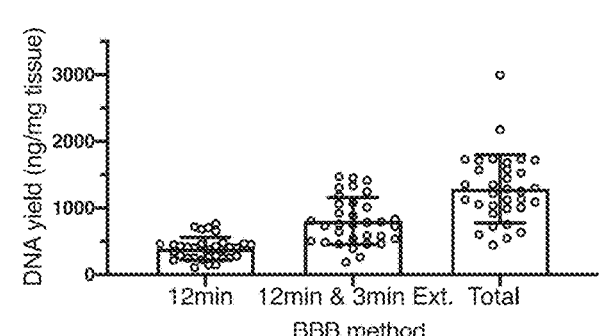

CVS sampling gDNA extraction (15min)

Library preparation (45min)

Sequencing (15min-2hr)

Data analysis (45min-1hr)

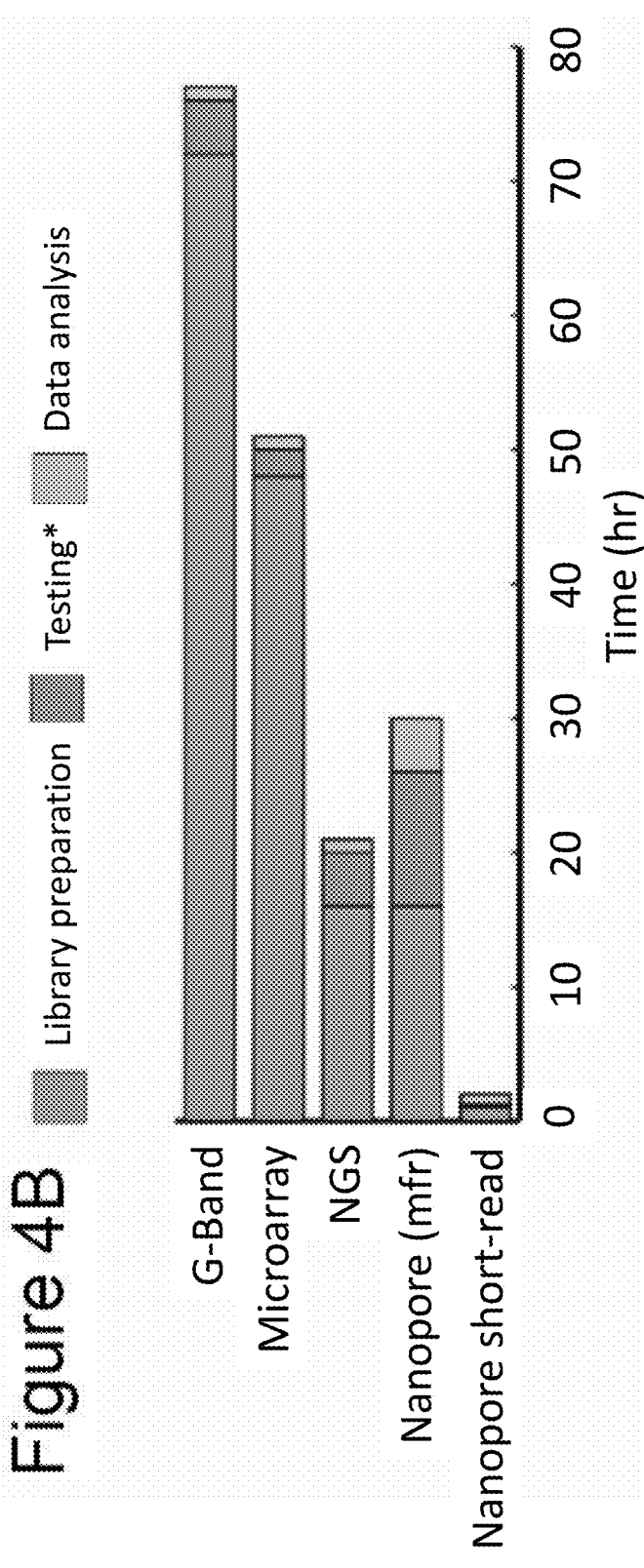

| Trisomy | Detection |
|---------|-----------|
| 100% | + |
| 50% | + |
| 40% | + |
| 30% | - |
| 20% | - |
| 0% | - |

Lane:
1. 1kb+ DNA ladder
2. gDNA
3. Pre-treated gDNA
4. Barcoded gDNA
5. Ligation product of lane 4 and 6
6. Sequence adapter Timeline:
- 15min gDNA extraction
- 10min tagmentation
- 25min purification
- 10min ligation Advantages:
- 65-85ng DNA from each sample
- 12 barcodes included
- <$100 per assay

METHODS FOR RAPID DNA EXTRACTION FROM TISSUE AND LIBRARY PREPARATION FOR NANOPORE-BASED SEQUENCING

CROSS-REFERENCE TO OTHER APPLICATIONS

The present application is a continuation of PCT/US2020/021395, filed Mar. 6, 2020, which claims priority to U.S. patent application Ser. No. 62/814,607 filed Mar. 6, 2019 and U.S. patent application Ser. No. 62/959,527 filed Jan. 10, 2020, both of which are hereby incorporated by reference in their entirety.

GOVERNMENT SUPPORT

This invention was made with government support under HD086327, awarded by the National Institutes of Health. The government has certain rights in this invention.

BACKGROUND

Nanopore-based DNA sequencing is a single-molecule-based, third generation, next generation sequencing (NGS) technology involving an array of protein pores arranged across a flow-cell membrane contained on a device weighing 87 grams and measuring 4.1×0.9×1.3 inches. Single strands of DNA are driven through protein pores by an electric field, and changes in electrical current are detected and translated into nucleotide identities as each nucleotide passes through the pore. Compared to second generation sequencing technologies, such as Illumina's MiSeq™ and NovoSeq™ and Thermo Fisher Scientific's Ion Proton™, nanopore sequencing has sequencing speeds 15,000-164,000-fold faster, enabling much quicker turn-around-times. Nanopore-based sequencing also has a low setup cost compared to second generation sequencing (less than $5000 versus about $50,000-$1,000,000) and requires only the disposable DNA sequencer and computer, instead of the large and complex next-generation sequencing machines.

While third generation NGS platforms were originally developed for sequencing long strands of DNA (greater than 8 kb and even greater than 1,000 kb), it was recently demonstrated that changes in the chemistry and library preparation could allow the device to be used for sequencing of short DNA reads (Wei and Williams 2016) and multiplexing (Wei, Williams and Weiss 2018; Wei et al. 2018a). However, library preparation for a single sample took 4 hours and multiple technically complex steps to complete. Sequencing took an additional 1-4 hours, and only a single sample could be sequenced at a time. These factors limited the clinical utility of the NGS sequencing platforms in such areas as prenatal genetic testing and cancer.

At its core, cancer is a disease of the genome. Consequently, identifying the specific genetic mutations that characterize tumors facilitates discovery of fundamental mechanisms of oncogenesis and chemoresistance, enables the creation of a new taxonomy of cancer that compliments existing histology-based classifications, and improves prognostication of clinical outcomes. Most critically, revealing the specific genetic vulnerabilities of the tumor allows the development and application of highly effective targeted therapies and combinatorial treatment approaches.

The field of basic and clinical cancer research is rapidly moving in this direction. The discovery of BRCA1 and BRCA2 mutations, activating mutations in the epidermal growth factor receptor (EGFR), and drugs targeting specific molecular abnormalities as exemplified by the BCR-ABL1 gene fusion, to list just a few, have highlighted the potential of this approach. Already, tumor DNA assessment using amplicon and hybrid-capture panels as well as ready-made vendor kit solutions are in use to better characterize individual tumors, guide treatment and enable "basket" trials that guide therapy selection based on genetic signatures (as opposed to traditional tissue classification). For example, BRAF V600 mutations, found in approximately half of cutaneous melanomas, are targets of four FDA-approved RAF and MEK inhibitors that have improved survival. While this mutation is common in cutaneous melanomas, over half of all BRAF V600 mutations occur in non-cutaneous melanomas including lung, thyroid and hairy cell leukemias. These same RAF and MEK inhibitors have been proven effective in these tumors too. Thus, selecting therapies based on genetic mutations will enable effective targeted therapies that would not have been considered based solely on the histological classification or primary tissue origin.

However, routine genomic study of every tumor at the point-of-care is currently not feasible due to the major technological limitation of the slow speed and high cost and complexity of existing sequencing technology. Testing takes weeks to months to complete and is available only at large cancer centers or through reference labs. This forces a severe restriction on recruitment of study subjects into clinical trials, running genome-driven clinical trials, more widespread characterization of genetic alterations, and universal implementation of precision oncology and precision treatments. For example, while there are over 57 academic and reference laboratories offering tumor panels with greater than 20 genes, the turnaround times range from 7-30 days, thereby requiring patients to choose between prompt initiation of traditional chemotherapy or delaying treatment to determine if targeting therapy would be an option. As a result, fewer patients are enrolled in clinical studies and benefit from targeted therapy. In addition, due to the high equipment start-up costs and complexity of library preparation and sequencing, only large academic and reference laboratories are able to offer this testing, thereby limiting its accessibility. Patients with a primary cancer diagnosis or with a recurrence are often faced with an agonizing decision—start traditional chemotherapy today or wait 4-12 weeks for the results of genetic profiling so that a targeted therapy can be initiated. In too many cases, the high cost of tumor profiling precludes this option altogether. Thus, there is a major feasibility gap that requires a highly novel and innovative solution to make precision oncology truly transformative in the clinical setting.

Consequently, creating technology that would enable widespread implementation of sequencing of tumor DNA will be transformative in both clinical care and research settings.

SUMMARY

The present disclosure includes improved novel methods for preparing, sequencing and analyzing short DNA fragments using handheld, nanopore-based sequencing technology.

Disclosed herein are new methods of DNA library preparation and sequencing using third generation nanopore sequencing that doubled the multiplexing capacity of a single run and reduced sequencing times by equal to or greater than 200%. In screening of both chorionic villus samples and pre-implantation genetic screening, the new methods were as accurate as traditional methods of screening for aneuploidy.

In some embodiments, the DNA is extracted from a biological sample. Biological samples include but are not limited to tissue, amniotic fluid, blood and urine. In some embodiments, the tissue is cancerous. In some embodiments, the tissue is from a fetus. In some embodiments, the tissue is from an embryo. In some embodiments, the tissue is from chorionic villus.

In some embodiments, the biological sample is cell culture.

In some embodiments, the DNA is genomic. In some embodiments, the DNA is an amplicon. In some embodiments, the DNA is cDNA.

In some embodiments, the DNA is extracted using a novel method which includes the following steps:

a. mixing or incubating the sample with BashingBead buffer and RNase A;

b. homogenizing the sample with BashingBead buffer and RNase A to create a mixture;

c. centrifuging the mixture and retrieving the supernatant;

d. mixing or incubating the supernatant with DNA binding buffer and loading on a spin column;

e. centrifuging the spin column of step d;

f. washing the spin column;

g. incubating the spin column with DNA elution buffer;

h. centrifuging the spin column; and i. retrieving the DNA.

In some embodiments, this entire method is performed in about 12 minutes.

In some embodiments, steps a. through c. are performed in about 8 minutes. In some embodiments, steps d. and e. are performed in about 30 seconds. In some embodiments, step f. is performed in about 30 seconds. In some embodiments, step f. is performed more than once. In some embodiments, steps g. through i. are performed in about 2.5 minutes.

In some embodiments, steps a. and b. are performed again or repeated prior to performing steps c. through i. except only BashingBead buffer is added in step a. In some embodiments, the repeated steps performed in about 30 seconds to about 3 minutes. In some embodiments, steps a. and b. are repeated one time. In some embodiments, steps a. and b. are repeated two times. In some embodiments, steps a. and b. are repeated more than two times, up to six times.

The second method disclosed herein is a novel method for library preparation for nanopore sequencing and is the so-called rapid direct ligation method. This method allows the use of the nanopore sequencing platform for shorter pieces of DNA including gDNA fragments, but also cDNA and amplicons. The rapid direct ligation allows a 15 minute to 2 hour sequencing read of about 2.0 million reads with a library preparation of about 45 minutes.

In some embodiments, the method for preparing or constructing a sequencing library for the high throughput nanopore sequencing comprises:

a. fragmenting the DNA extracted or obtained from a sample;

b. end preparing the fragmented DNA;

c. ligating the DNA to a barcode;

d. pooling the barcoded DNA;

e. purifying the pooled barcoded DNA; and f. ligating a sequence adaptor to the pooled barcoded DNA.

The entire library preparation takes about 45 minutes.

In some embodiments, the DNA is extracted from a biological sample. Biological samples include but are not limited to tissue, amniotic fluid, blood and urine. In some embodiments, the tissue is cancerous. In some embodiments, the tissue is from a fetus. In some embodiments, the tissue is from chorionic villus. In some embodiments, the DNA is extracted using any method known in the art. In some embodiments, the DNA is extracted using the novel method set forth herein. In some embodiments, the tissue is from an embryo. In some embodiments, the cells or DNA from an embryo are amplified by standard methods.

In some embodiments, the DNA is genomic. In some embodiments, the DNA is an amplicon. In some embodiments, the DNA is cDNA.

The next step of the method is sequencing the samples. The resulting sequencing library is loaded on a nanopore sequencing device and the reaction run for about 15 minutes to about 2 hours. About 2,000,000 reads are generated using this method.

The last step of the method is the data analysis which takes about 30 minutes to an hour.

The third method disclosed herein is another novel method for library preparation for nanopore sequencing and is the so-called tagmentation-based rapid method or rapid tag. This method allows the use of the nanopore sequencing platform for shorter pieces of DNA including gDNA fragments, but also cDNA and amplicons. This method allows about 900,000 reads in 2 hours with a library preparation of about 45 minutes.

Thus, a further embodiment is a method of preparing or constructing a sequencing library for high throughput nanopore sequencing comprising:

a. fragmenting the DNA extracted or obtained from a sample;

b. incubating the fragmented DNA with a barcoded Tn5 enzyme;

c. purifying and pooling the DNA barcoded by Tn5; and d. ligating the barcoded Tn5 DNA to a BAM 1D sequence adaptor in a purification-free ligation reaction.

The entire library preparation takes about 45 minutes.

In some embodiments, the DNA is extracted from a biological sample. Biological samples include but are not limited to tissue, amniotic fluid, blood and urine. In some embodiments, the tissue is cancerous. In some embodiments, the tissue is from a fetus. In some embodiments, the tissue is from chorionic villus. In some embodiments, the DNA is extracted using any method known in the art. In some embodiments, the DNA is extracted using the novel method set forth herein. In some embodiments, the tissue is from an embryo. In some embodiments, the cells or DNA from an embryo are amplified by standard methods.

In some embodiments, the DNA is genomic. In some embodiments, the DNA is an amplicon. In some embodiments, the DNA is cDNA.

The next step of the method is sequencing the samples. The resulting sequencing library is loaded on a nanopore sequencing device and the reaction run for about 15 minutes to about 2 hours. About 900,000 reads are generated using this method.

The last step of the method is the data analysis which takes about 30 minutes to an hour.

The current disclosure also provides for kits for performing any of the methods disclosed herein for DNA extraction, library preparation and the like.

BRIEF DESCRIPTION OF THE DRAWINGS

For the purpose of illustrating the invention, certain embodiments of the invention are depicted in drawings.

However, the invention is not limited to the precise arrangements and instrumentalities of the embodiments depicted in the drawings.

FIG. 2 shows the results of the comparison of the various DNA extraction protocols. FIG. 2A shows the comparison of gDNA purified using two β-mercaptoethanol (ME)-free protocols by gel electrophoresis. Two tissue samples (A&B) were purified using the Quick-DNA insect/tissue kit protocol (Mfr) and DNA clean & concentrator-5 protocol (Rapid). FIG. 2B is a gel image of gDNA extracted from chronic villi tissue samples using the rapid and extended BBB extraction protocols. Tissue samples (sample 1-4) were subjected to the rapid BBB method as well as a 3- and 6-minute extension. FIG. 2C shows the evaluation of impact of bead-bashing process towards the integrity of gDNA. Technical repeats of gDNA treated for 3 min, 5 min and 10 min bead bashing times. FIG. 2D is a graph of gDNA yields using rapid and extended BBB methods. gDNA yield from each individual sample is shown in dots, the bar graph indicated the mean±SD.

FIG. 4 is an overview and results of the use of the rapid nanopore sequencing method for aneuploidy screening of chorionic villus (CVS) samples. FIG. 4B is a comparison of the time required for aneuploidy screening assay using G-band karyotyping, microarray, next generation sequencing (NGS), the manufacturer's approach to nanopore sequencing (mfr), and nanopore short-read sequencing. *Testing represents the staining step in G-band karyotyping, the washing step in microarray testing, and sequencing in NGS and nanopore testing.

DETAILED DESCRIPTION

Figure 1:
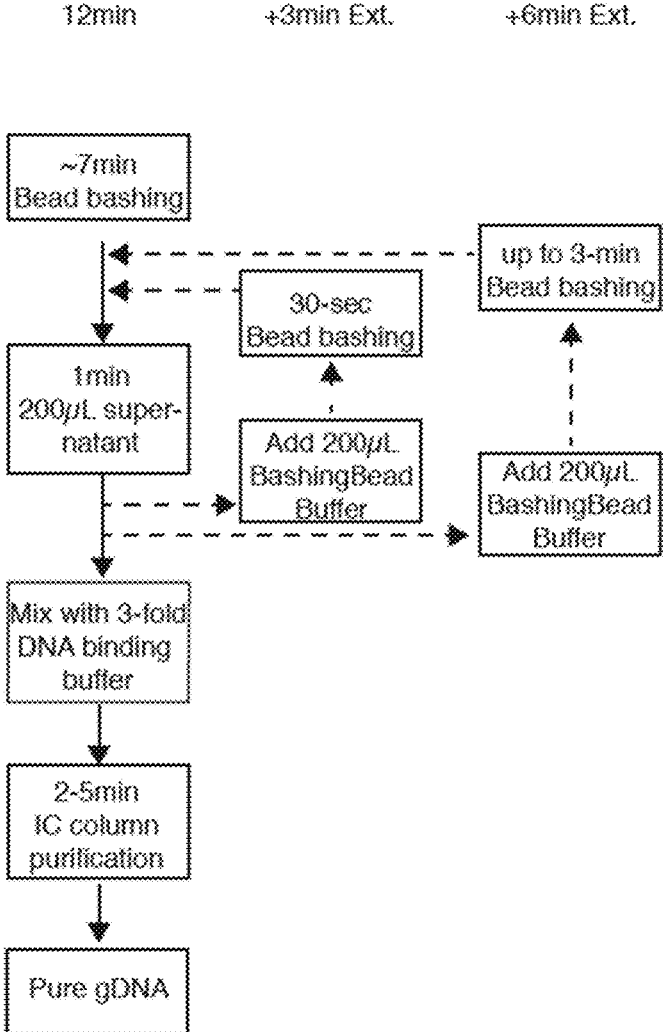
FIG. 1 shows the workflow of the 12-minute rapid Bead Bashing based (BBB) extraction protocol and the 3-minute and 6-minute extension.

Next-generation sequencing (NGS) is critical for target sequencing. Shown herein are methods of nanopore sequencing using a handheld third generation sequencing platform for rapid clinical applications. Nanopore sequencing, which detects electric current characteristics of a single oligonucleotide molecule as it passes through a nano-size protein channel, does not require time-consuming base-by-base biochemical reaction of traditional NGS platforms such as Illumina and Ion Proton. Nanopore sequencing was initially developed by Oxford Nanopore Technologies (ONT) to perform ultra-long-read sequencing (6 Kb-1 Mb) on a $500 disposable flowcell. Many clinical applications of interest, such as preimplantation genetic screening (PGS) and target sequencing do not require ultra-long sequencing. However, the manufacturer's protocol of nanopore sequencing cannot be simply adapted to perform short-read nanopore sequencing (less than 1 kb), which is the major read length spectrum of most established NGS applications. Because the manufacturer's protocol failed to produce a successful short-read nanopore sequencing library, and could not be applied to many clinical applications, the inventors systemically investigated, innovated and optimized each step of performing short-read sequencing on nanopore sequencing and developed robust and rapid library preparation methods.

The result improved methods of preparing DNA for nanopore sequencing.

Also disclosed herein is a novel improved method for the extraction of genomic DNA from tissue based upon bead-bashing which produces cleaner DNA in less time without the use of beta-mercaptoethanol which would necessitate that all downstream procedures to be carried out in a chemical fume hood and has a strong odor and adds significant hands-on time to the actual workflow.

Improved Method for Extracting High Quality Genomic (gDNA) from Biological Samples Including Mammalian Tissue ("Rapid Bead-Bashing Based (BBB) Extraction or Method")

Extracting high quality genomic DNA (gDNA) from a biological sample is the first step for many molecular genetics studies and clinical diagnostic tests (Zhang et al. 2015; Carp et al. 2006; Levy and Wapner 2018). For rapid genetic clinical tests, such as qPCR, PCR-based genotyping and nanopore-based sequencing, the DNA extraction step is now the most time-consuming component of the workflow and adds significant time to the testing (Zhang et al. 2015; Wei and Williams 2016; Wei, Williams and Weiss 2018a) Extraction of gDNA from mammalian tissue typically uses detergents and/or enzymes to lyse cell and nuclear membranes and provides DNA yields of approximately 0.2 to 3 μg gDNA per mg tissue, depending on the tissue (Tomaso et al. 2010). However, the lysis step requires 2-12 hours to complete. Because incomplete lysis will lead to a decrease in DNA yield and an overnight lysis step leads to higher gDNA yields without decreasing DNA quality, the standard protocol for many basic and clinical labs is to use overnight lysis to ensure the quality and yield of gDNA extracted from mammalian tissues. Liquid nitrogen and tissue disruption using a syringe have also been used to enhance the homogenization of human tissue samples and shorten processing times (Pajnic 2016). However, these require more hands-on time, have a low throughput, and are not amenable to automation. While traditional bead-bashing methods for DNA extraction have been applied to samples that are difficult to extract, such insect cells (Marr et al. 2018), they have required the use of β-mercaptoethanol (β-ME), a fume hood, and a more complex multi-step procedure using multiple DNA purification columns, which is impractical for use with automation and in a clinical setting.

Disclosed herein is a simplified bead-bashing based (BBB) gDNA method for rapidly extracting high quality gDNA from biological samples including mammalian and human tissue. This simplified workflow streamlines the gDNA extraction process and provides sufficiently high quality gDNA for urgent diagnostics assays in under 15 minutes. An enhanced workflow also provides more than triple the gDNA yield to accommodate applications requiring higher input DNA quantities.

The rapid BBB methods showed good results on gDNA extraction from human soft tissue performed in under 20 minutes. The 12-minute rapid BBB method yielded sufficiently large size (greater than 15 kb) gDNA for applications that require 100 ng gDNA or less. The 3- and 6-minute extensions recovered more gDNA from the same specimen to accommodate applications that requires sub-μg to μg-level gDNA input. The rapid BBB based gDNA extraction method significantly reduced the time, complexity and equipment required to extract high quality gDNA from tissue and allowed urgent gDNA-based diagnostic tests to be carried out in a timely manner. The BBB gDNA extraction method thus provides a simple, robust and rapid method for gDNA extraction from mammalian tissue that reduces the number and duration of centrifugation steps, uses only a single purification column instead of multiple columns and one wash buffer instead of multiple buffers, eliminates the need for β-mercaptoethanol (β-ME) and a fume hood and is amenable to automation and time-sensitive clinical applications.

The rapid BBB method can be used to extract DNA from any biological sample including any tissue from any type of mammal. A biological sample also includes cell culture.

Biological samples include but are not limited to tissue, amniotic fluid, blood and urine. In some embodiments, the tissue is cancerous. In some embodiments, the tissue is from a fetus. In some embodiments, the tissue is from an embryo. In some embodiments, the tissue is from chorionic villus.

Other tissue includes but is not limited to musculoskeletal tissues, arteries and blood vessels, and organs. Organs include but are not limited to heart, lungs, liver, kidney, intestines, and epidermis.

Mammals include but are not limited to canines, felines, rodents, bovine, equines, porcines, ovines, and primates including humans.

In some embodiments, the DNA is genomic.

The novel method for efficiently extracting DNA includes the following steps.

The first step is to incubate the sample with BashingBead buffer which contains edetate disodium, dihydrate and trometamol as the active ingredients. The buffer is used in an amount ranging from about 400 μL to about 800 μL, or an amount ranging from about 450 μL to about 750 μL, or an amount ranging from about 500 μL to about 650 μL, or an amount of about 550 μL.

RNase A is also added to the sample in this step. The RNase A can be in a concentration of about 20 mg/ml and added in an amount of about 10 μL.

The sample and the buffer and RNase A are then homogenized by any method known in the art to obtain a homogenized mixture. In the exemplified method, a Bead Bashing lysis tube is used. This step is performed in about 7 minutes.

The mixture is then centrifuged at a speed and for a time sufficient to retrieve supernatant containing enough DNA for the next step which is incubating the supernatant with DNA binding buffer.

These steps of incubating, homogenizing and centrifuging are performed in about 8 minutes.

When these steps are performed once, approximately 0.4 μg of DNA per milligram of tissue with a range of about 0.11 to about 0.77 μg are retrieved from about 200 μL of supernatant. See Table 1. This amount of gDNA is sufficient for downstream applications such as qPCR, MLAP, microarray analysis, and nanopore sequencing, and produces similar yields as the manufacturer's protocol but is less time and in a much more streamlined and convenient fashion.

If more DNA is needed for the downstream analysis, these steps can be repeated. In some embodiments, the steps are repeated one time. In some embodiments, the steps are repeated two times. In some embodiments, the steps are repeated more than two times, up to six times.

When repeated, additional BashingBead buffer only is added to the tube with the original mixture, in an amount ranging from about 100 μL to about 500 μL, or an amount ranging from 150 μL to about 450 μL or an amount of about 400 µL, or an amount of about 200 µL. The mixture is then homogenized by any method known in the art to obtain a homogenized mixture. The mixture is then centrifuged at a speed and for a time sufficient to retrieve supernatant containing enough DNA.

The repeated steps take about 30 seconds to about 3 minutes and can be repeated once for a total time of about 30 seconds to about 3 minutes or twice for a total time of about 1 minute to about 6 minutes. The steps can be repeated more than twice up to six times.

When these steps are repeated once, approximately 0.43 µg of DNA per milligram of tissue with a range of about 0.08 to about 1.05 µg are retrieved. When these steps are repeated twice, approximately 0.48 µg of DNA per milligram of tissue with a range of about 0.16 to about 2.45 µg are retrieved. See Table 1. This amount of gDNA is sufficient for downstream applications such as whole genome sequencing, genotyping and other downstream analysis.

The next step of the method is mixing the supernatant containing the DNA retrieved from the first step performed once or repeated, with DNA binding buffer. It is preferred that the DNA binding buffer is a guanidinium chloride based-binding buffer. The DNA binding buffer can be added in about a 3-fold volume and then loaded on a spin column. The spin column is then centrifuged for about 30 seconds, and subsequently washed with DNA wash buffer. It is preferred that the wash buffer contain 2-amino-2-(hydroxymethyl)propane-1,3-diolhydrochloride, edetate disodium, dihydrate, and 80% ethanol. This step can be repeated.

The column which now contains the ultrapure gDNA is incubated with DNA elution buffer for about 1 to about 3 minutes and centrifuged to obtain the final gDNA. The DNA elution buffer can contain is 10 mM Tris-HCl, pH 8.5, and 0.1 mM EDTA.

As shown in FIG. 3C, the quality of the gDNA obtained from the novel method is of high quality. Also as shown, sufficient quantities of gDNA are obtained for all downstream applications using the novel method which is a shorter, more streamlined, convenient method which does not require a hood.

Also provided herein are kits for practicing the improved method of DNA extraction. The kit could include but is not limited to BashingBead buffer, RNase A, DNA binding buffer, DNA wash buffer, and DNA elution buffer in amounts needed to perform the method, as well as vials or other containers for the various mixtures, and spin columns. This kit may additionally include one or more reagents or instruments which enable any of the embodiments of the method to be carried out. In addition, kits would also further include instructions.

Improved Method for Library Preparation, Sequencing and Data Analysis using Hand-Held Nanopore-Based DNA Sequencing ("Rapid Direct Ligation Method")

The method disclosed herein for nanopore sequencing is a ligation-based barcoding nanopore sequencing method. DNA fragments are subjected to end preparation and direct ligation to barcode adapters. The barcoded ligation products are pooled and purified and subject to a purification-free final ligation to nanopore sequencing adapter, and ready for sequencing.

It is a streamlined and least manufacturer dependent ligation-based barcoded protocol for short-read nanopore sequencing.

Four limitations that previously precluded clinical application of nanopore-based sequencing for providing same-day results were systematically addressed by the new method.

1. The manufacturer's protocol enables sequencing of long reads, which, while useful in genome assembly, does not generate sufficient numbers of individually mapped short reads necessary for rapid diagnosis and requires a complex series of library preparation steps. The modified and simplified library preparation enables higher throughput sample preparation and sequencing of greater numbers of shorter reads.

2. Introduction of graphics processing unit (GPU)-based basecalling enabled a 20-fold increase in speed compared to the manufacturer's basecalling algorithm.

3. Some of the barcodes provided by the manufacturer have 40-50% fewer reads assigned than the average, thus requiring nearly double sequencing time for the samples assigned to these barcodes. In this method, custom-designed barcodes are used that reduced the CV of reads assigned to each barcode from 38.4% to 4.8% and reduced batch effects (Wei, Weiss and Williams 2018)

4. The original data analysis pipeline relied on the computationally-heavy parallel BLAST-like alignment tool (BLAT), a pairwise sequence alignment algorithm (Wang and Kong 2019; Kent 2002). While faster alignment tools exist (e.g. bowtie2 and minimap2), BLAT was still the most sensitive aligner for nanopore short-reads and gave the lowest false positive detection rate during development. To accelerate the alignment process, a multi-thread approach was employed on up to 96 CPU cores to keep the alignment process under 30 minutes (Wei, Williams and Weiss 2018). This approach costs $2-$5 per sample cost for the acquired computational resources.

Because of the low initial capital costs of the flow cells (less than $5000) and small footprint compared with next generation sequencing platforms (often greater than $250,000) this technology is amenable to point-of-care testing, thus avoiding the time and cost required to transport samples to a centralized laboratory. Use of barcoding and multiplexing reduced the cost of the flow cell proportionally from $100 to $50 per sample when compared to previous studies reported barcoded up to 5 samples in a run (Wei et al. 2018a; Wei, Weiss and Williams 2018). The flow cells can be reused for four runs, further reducing the flow cell costs to $12.50 per sample. The reagent costs for DNA extraction and library preparation is under $20 per sample, making up the cost of assay per sample to under $32.50 (Wei et al. 2018a). For urgent cases where only one sample is sequenced, up to $600 reagent cost may incur, and the testing results can be delivered within two hours from sample receipt. Nanopore-based aneuploidy screening also has higher throughput, shorter turnover time, and lower labor requirement than microarray and G-banding karyotyping, which will reduce the cost on labor for processing the same scale of samples (Levy and Wapner 2018).

In summary the innovations of Rapid Direct Ligation Nanopore Sequencing are as follows:

1. Shorten the workflow. The library preparation eliminated the time-consuming purification, quantification and normalization step after DNA end preparation in conventional library preparation. It reduced the library preparation workflow to about 45 minutes. It is especially advantageous when handling multiple samples.

2. Broad applications. The method is suitable to prepare nanopore-sequencing library for PCR amplicons, cDNA and short gDNA fragments.

3. Low cost. The reagent cost for each sample is about $20. The total cost of the assay including sequencing cost per sample is under about $32 if samples were multiplexed on one nanopore flowcell.

4. Reduced DNA input. The method uses a highly efficient purification/size-selection step after barcode ligation and has only one purification step in the entire library preparation workflow. Greater than 80% DNA input will end up in a final library, which significantly reduced the required DNA input. About 0.4 pmole short DNA fragments from each sample are needed for library preparation.

5. Stable performance of barcodes. A set of in-house designed barcodes was used in the direct-tag method to barcode multiple samples. Comparing to manufacturer's barcodes, the standard deviation of number of sequences assigned to each barcode is significantly lower and the mean is higher, i.e., higher coverage on each sample even the total sequencing yields were similar.

6. Better barcode quality control. The in-house barcode adapters also have improved quality control.

7. A high-yield nanopore sequencing library. The library prepared using this method resulted in greater than about 2.0 M reads in 2 hours. It is sufficient to perform aneuploidy detection on at least 12 samples.

The first step of the method of library preparation or construction is extracting the DNA from the sample. Any method known in the art can be used. In some embodiments, the method for DNA extraction set forth herein is used.

The next step is to fragment the DNA obtained from the extraction. The nucleic acids from the sample are subjected to fragmentation, to obtain a nucleic acid fragment. There are no special limitations on a type of the nucleic acid sample which may be used and there are no special limitations on means for performing the fragmentation; and any chemical or physical methods which may make nucleic acid samples subjected to randomly fragmentation may be used to randomly fragment the nucleic acid sample. While any size fragments can be used, the improved method is used for shorter read nanapore sequencing. Thus, the size of the fragments is about 1000 bp or less, or about 900 bp or less, or about 800 bp or less, or about 700 bp or less, or about 600 bp or less, or about 500 bp or less.

The next step of the method is end preparing the fragmented DNA. One advantage of the current method is that there is no time-consuming purification, quantification and normalization step after DNA end preparation as found in conventional library preparation. Also reducing the volume of the end preparation reaction improves the efficiency of the two-end ligation. About 10 µL of about 5 ng/µL fragmented DNA is incubated with about 2 µL of repair master mix which contains at least repair buffer and repair enzyme mix. The master mix contains about 2:1 buffer to enzyme mix. The enzyme mix can contain one or more DNA polymerases and Klenow fragment. The reaction takes place for a time and at a temperature to allow the ligation to occur, usually in about 12 minutes.

Using this reduced volume and master mix, the end-repairing reaction could be performed in about 12 minutes with about 80% two-end ligation products as opposed to about one hour for standard methods, and no purification, quantification or normalization step is needed after this step.

The next step of the method is ligating the end prepared DNA to a barcode. The barcodes used are a set of in house designed barcodes which improve coverage and quality control. In some embodiments, such as those used for maternal and reproductive applications, the barcodes are about 34 bp, have compatible ends for nanopore library preparation, and have a Tm ranging from about 58° C. to about 63° C. In some embodiments, such as those used for cancer, the barcodes are about 118 bp. See Tables 2 and 9.

The ligation reaction is performed by adding the barcodes in a concentration of about 10 µM to 50 µM, or about 10 µM to 20 µM, to the end prepared reaction in an amount of about 0.2 µL, to about 2 µL, or an amount of about 1 µL, or an amount of about 0.5 µL. A ligase master mix is also added to the mixture. The ligase master mix can contain T4 DNA ligase, Tris-HCl, MgCl₂, dithiothreitol, ATP, and polyethylene glycol (PEG 6000 or PEG 8000).

The reaction takes place for a time and at a temperature to allow the ligation to occur, usually in about 10 minutes.

All of the reactions are then pooled for the only purification step in the process. This single purification step is another improvement on time and efficiency of the disclosed method. Not only does this allow the entire preparation to be performed in less time, less DNA is needed to start because greater than 80% of DNA input will be in the final library. The purification step can be performed by any method known in the art.

In the exemplified method, the pooled reactions were purified by loading on a spin column, washing and eluting the DNA. The concentration of the recovered DNA was then determined.

The last step of the method is the final ligation of the purified pooled barcoded DNA to a sequence adaptor. In some embodiments, the adaptor has a compatible sticky end. In some embodiments, the adaptor is a linear adaptor. In some embodiments, the adaptor comprises an identifier sequence.

The exemplified method uses the Nanopore Adaptor as well as the enhancer mix and buffer. The enhancer mix can contain MgCl₂ and ATP.

Figure 3:
FIG. 3 is a representative gel image of a sample library using the rapid direct ligation method. Lane 1 shows the barcoded DNA; Lane 2 shows the final library; Lane 3 shows the nanopore sequencing adaptor; Lane 4 shows the 1kb+DNA ladder. A 3% gel, at 180 V for 30 minutes was used. After the final ligation, barcoded DNA was sufficiently ligated to the nanopore sequencing adaptor, causing a significant shift in Lane 2. There was no visible unligated nanopore sequencing adaptor in the final library as shown in Lane 2.

The adaptors were reconcentrated to reduce technical variations and batch effects (Wei and Williams 2016; Wei, Williams and Weiss 2018a). This step is performed in about 10 minutes. As shown in FIG. 3, ligation products for nanopore sequencing were successfully obtained using this method. Moreover, the library prepared using this method resulted in greater than about 2.0 M reads in 2 hours.

Analysis of the data collected is also improved using the method disclosed in Wei, Williams and Weiss 2018, and is performed in about 30 minutes to an hour.

The method was used successfully for aneuploidy testing in genomic DNA samples. Using this method, up to twelve samples can be multiplexed to produce sufficient sequencing data for aneuploidy detection in about 1-3 hour on a single flow cell, including library preparation time. If the rapid DNA extraction method disclosed herein is used, there is an additional 12 minutes as opposed to an additional 1-3 hour for conventional gDNA extraction from human tissues or body fluids. There is also another 30 minutes for computational analysis in the development phase, making the entire time needed for testing in some instances under 2 hours and in most instances less than 4 hours.

Also provided herein are kits for practicing the improved method of library preparation. The kit could include but is not limited to end repair master mix, barcodes, reagents needed for purifying the pooled DNA, adaptors, and various buffers in amounts needed to perform the method, as well as vials or other containers for the various mixtures, and spin columns. This kit may additionally include one or more reagents or instruments which enable any of the embodiments of the method to be carried out. In addition, kits would also further include instructions.

Improved Method for Library Preparation, Sequencing and Data Analysis using Hand-Held Nanopore-Based DNA Sequencing ("Tagmentation-based rapid nanopore sequencing or Rapid-Tag")

Also disclosed herein is another improved method for nanopore sequencing including library preparation, sequencing and data analysis denoted tagmentation-based rapid nanopore sequencing or rapid-tag.

As shown herein, using this method, short (less than 1000 nt, approximately 400 nt) DNA strands were successfully sequenced 15,000 to 27,000-fold faster than an Ion Proton, and 162,000-fold faster than an Illumina MiSeq. To enable successful short-read nanopore sequencing, end-repair efficiency was improved from approximately 30% to approximately 80%; ligation efficiency of TA ends from 75.6% to 93.2%, and 6-bp sticky ends from 94.9% to 97.2%; and tethering efficiency from approximately 50% to >95%. The workflow was simplified from an 80-minute manufacturer protocol to a 45 minute rapid protocol.

In summary the innovations of tagmentation-based rapid nanopore sequencing are as follows:
1. In-house designed 8 bp short barcodes in contrast to manufacturer's 34 bp long barcodes for accurate multiplexing for nanopore sequencing. Approximately 70% reads can be assigned to a specific sample according to short barcodes, which is comparable to the performance of long barcodes.
2. Short barcodes can perform much more efficient tagmentation using Tn5 transcriptase comparing to manufacturer's long barcodes using MuA transcriptase. Tn5 is more efficient in tagmentation than MuA, but it can only carry a short duplex without reducing the efficiency. The short barcodes made it possible to use Tn5 for tagmentation in contrast to the long barcode.
3. Efficient purification condition after the Tn5 tagmentation. It is known that Tn5 binds tightly to DNA during the tagmentation and the purification efficiency was low. The purification efficiency was increased from approximately 40% to greater than 85%. This is very helpful in reducing the required gDNA inputs and reagents. Currently 65-85 ng gDNA and 1.2-1.4 units of Tn5 are needed from each sample to perform the tagmentation-based rapid nanopore sequencing library preparation.
4. In-house conditions for concentrating the BAM 1D sequencing adapter to 10×and storing for 2 months without losing motor protein's function. The manufacturer's sequencing adapter BAM 1D comes in 100-200 nM, and the storage buffer is proprietary. The adapters were concentrated to 10×and stored it in in-house developed storage buffer without reducing its activity.
5. An in-house purification-free ligation condition to ligate the tagmentation products directly to the concentrated sequencing adapter without an extra purification step. It reduced the library preparation time by 20 minutes and eliminated the DNA loss during an extra purification. The ligated products are nanopore sequencing compatible and can be loaded to the sequencer directly. It is also very inexpensive, less than 50 cents are needed for the ligation.
6. A high-yield nanopore sequencing library. The library prepared using this method resulted in greater than 900K reads in 2 hours. It's sufficient to perform aneuploidy detection on at least 12 samples.

The first step of the method of library preparation or construction is extracting the DNA from the sample. Any method known in the art can be used. In some embodiments, the method for DNA extraction set forth herein is used.

The next step is to fragment the DNA obtained from the extraction. The nucleic acids from the sample are subjected to fragmentation, to obtain a nucleic acid fragment. There are no special limitations on a type of the nucleic acid sample which may be used and there are no special limitations on means for performing the fragmentation; and any chemical or physical methods which may make nucleic acid samples subjected to randomly fragmentation may be used to randomly fragment the nucleic acid sample. While any size fragments can be used, the improved method is used for shorter read nanapore sequencing. Thus, the size of the fragments is about 1000 bp or less, or about 900 bp or less, or about 800 bp or less, or about 700 bp or less, or about 600 bp or less, or about 500 bp or less.

The next step of the method is incubating the fragmented DNA with a barcoded Tn5 enzyme. A set of Tn5 compatible barcoded duplexes were designed using barcodes of about 8 bp and have a Tm of about 54.5° C. to about 59° C. The duplexes can be made by any method known in the art. These duplexes are compatible with both the Tn5 transposase and the BAM 1D sequencing adaptor. See Table 11.

The barcoded TN5 enzyme is then prepared by incubating Tn5 transposase with the barcoded duplexes for a time and at a temperature to allow the reaction to occur.

The fragmented DNA from the sample is then incubated with the barcoded Tn5 enzyme in a tagmentation reaction system. The tagmentation reaction system includes but is not limited to the DNA, the Tn5 barcoded enzyme, T9 buffer and elution buffer. The total tagmentation reaction system is about 10 μL to about 30 μL, or about 15 μL to about 25 μL. The amount of DNA added to the system ranges from about 20 ng to about 90 ng, or about 45 ng to about 85 ng, or about 65 ng to about 85 ng. Approximately 1.0 to about 2.0 units of Tn5 or about 1.2 to about 1.8 units of Tn5 are used in the reaction. As stated above the efficient purification conditions allow less DNA and less Tn5 to be used in the tagmentation reaction.

The reaction takes place for a time and at a temperature to allow the tagmentation to occur.

The reaction can then be quenched using any method known in the art.

The Tn5 barcoded DNA are then pooled for the only purification step in the process. This single purification step is another improvement on time and efficiency of the disclosed method. Not only does this allow the entire preparation to be performed in less time, less DNA is needed to start because greater than 85% of DNA input will be in the final library. The purification step can be performed by any method known in the art.

The last step of the method is ligating the Tn5 barcoded DNA to a BAM 1D sequencing adaptor. The BAM 1D is concentrated about 10-fold. The ligation is purification-free and the reaction can comprise the barcoded DNA, the 10-fold BAM 1D, ligation master mix and an enhancer mix. The enhancer mix can contain $MgCl_2$, ATP, and Tris buffer.

The reaction takes place for a time and at a temperature to allow the ligation to occur.

The entire method takes about 45 minutes.

Figure 11:
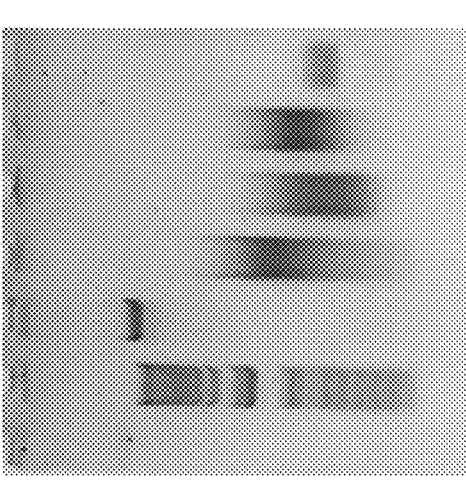
FIG. 11 is an agarose gel showing a representative ligation product using the tagmentation method for a MinION sequencing library. Lane 1 is a 1 kb+DNA ladder; Lane 2 is the extracted gDNA; Lane 3 is the pre-treated gDNA; Lane 4 is the barcoded gDNA; Lane 5 is the ligation product of Lanes 4 and 6; and Lane 6 is the sequence adaptor.

As shown in FIG. 11, ligation products for nanopore sequencing were obtained using this method. Moreover, the library prepared using this method resulted in greater than about 900,000 reads in 2 hours.

Analysis of the data collected is also improved using the method disclosed in Wei, Williams and Weiss 2018a, and is performed in about 30 minutes to an hour.

The method was used successfully for aneuploidy testing in genomic DNA samples. Using this method, up to twelve samples can be multiplexed to produce sufficient sequencing data for aneuploidy detection in about 2 hours.

Also provided herein are kits for practicing the improved method of library preparation. The kit could include but is not limited to Tn5 barcoded DNA or the barcoded DNA, Tn5 enzyme and reagents for preparing the Tn5 barcoded DNA, reagents needed for purifying the pooled DNA, BAM 1D adaptors, and various buffers in amounts needed to perform the method, as well as vials or other containers for the various mixtures. This kit may additionally include one or more reagents or instruments which enable any of the embodiments of the method to be carried out. In addition, kits would also further include instructions.

Uses of the Methods

The improved methods of extraction of DNA from tissue, library preparation and sequencing can be used in a variety of applications related to reproductive and maternal health including but not limited to aneuploidy screening from chorionic villus samples and amniotic samples, preimplantation genetic testing (PGT) and screening (PGS) for in vitro fertilization procedures, and screening of miscarried embryos (products of conception (POC)). The improved methods can also be used for cancer screening.

Aneuploidy Screening in Chorionic Villus Samples

Fetal aneuploidy is a common cause of pregnancy loss, structural anomalies, developmental delays and the primary reason that patients undergo prenatal diagnostic testing (Chiu et al. 2008). Existing methods for prenatal testing of all chromosomes involve examination of chronic villi sampling (CVS) or amniocentesis samples using G-banding karyotyping, microarray, or next-generation sequencing (Levy and Wapner 2018), and FISH and MLPA for testing a subset of chromosomes (Carp et al. 2006; Fragouli et al. 2011). Non-invasive prenatal testing (NIPT) is now also commonly used to screen for trisomy 13, trisomy 18, and trisomy 21 using next generation sequencing (Bianchi and Parker 2014; Norton et al. 2015). However, these approaches require processing patients' samples at centralized clinical reference laboratories and performing the tests on complex and costly equipment, thereby increasing costs for testing and reducing access. In addition, the turn-around times for the existing methods range from 24 hours to four weeks, thereby delaying possible clinical intervention and increasing patient waiting and anxiety. Thus, a low-cost, point-of care method for prenatal testing of CVS samples that could be provide results on the same day would improve clinical care and access to treatment The improved methods of nanopore-based library preparation (both direct tag and rapid tag) and sequencing were used to test for aneuploidy in chorionic villus samples (CVS).

In one study using direct tag, blinded CVS samples from women (n=52) who underwent chorionic villus sampling (CVS) and G-band karyotyping as part of their routine clinical care were subjected to a novel DNA extraction, DNA library preparation, nanopore sequencing, and data analysis using the methods disclosed herein. Whole-genome, low-coverage (0.01×) nanopore-based DNA sequencing was performed and sequenced reads were aligned to the genome. A custom-designed data analysis pipeline was used to determine ploidy and detect copy number variations (CNV). Nanopore-based results were then compared with the results obtained from standard G-band karyotyping.

The results showed that the sequencing rate ranged from 13,413-17,044 reads/min, with 1.61-2.05M reads obtained in 2 hours, sufficient to diagnose aneuploidy with sequencing times of 10 minutes for a single sample or 2 hours for 12 multiplexed samples. Furthermore, the results of testing by nanopore-based sequencing of extracted DNA were 100% concordant with blinded G-band karyotyping results across all samples and consisted of 29 euploid male, 13 euploid female, 7 trisomy, 2 mosaic trisomy and a 38 MB CNV (gain). The total time required for the workflow was about 4 hours, consisting of 15 minutes for DNA extraction, 45 minutes for library preparation, 15 minutes to 2 hours for sequencing and 1 hour for analysis, and without the need to culture cells. The cost of the assay was about $32.50 to about $70.00 per sample when multiplexed samples were used.

In another study using rapid tag, three runs were performed where about 700,000 to about 950,000 reads were generated in about 2 hours. The detection of aneuploidy was in 100% agreement with the results of G-band karyotyping.

It was concluded that the improved methods of nanopore-based aneuploidy testing can accurately detect aneuploidy and large CNV in CVS samples in under four hours, at low cost, at point of care, and without the need to culture samples. The sensitivity and specificity of aneuploidy and large CNV in tissue from CVS were both 100% compared to the results from standard G-banding karyotyping method.

Pre-Implantation Embryo Screening

The improved methods of nanopore-based library preparation and sequencing were used to test for aneuploidy in embryo samples. Normally in embryo screening 3-5 cells or picogram levels for DNA are obtained from the embryo. The DNA can be cell-free DNA from media. The cells or DNA can be subjected to DNA amplification directly to generate microgram to sub-microgram levels of DNA for the assay. When used for embryo screening, the DNA can be amplified using any method known in the art including but not limited to PicoPlex or MALBAC. This is a further advantage of the disclosed method in that DNA amplified by any method can be sequenced efficiently.

In 2 hours, a total of 1.36-1.68M reads were obtained, comprising 1.22-1.50M high quality reads. The amount of time required from tissue to results was 2-4 hours for the nanopore-based aneuploidy screening, depending on the number of samples multiplexed. The sensitivity and specificity of large CNV in embryo tissue were both about 100% compared to the results from standard G-banding karyotyping method. The specificity was 100% and sensitivity was 89% for full aneuploidy and 50% for mosaic aneuploidy as compared to standard G-banding karyotyping method.

Products of Conception Screening

Miscarriage is a prevalent condition that occurs in approximately 30% of pregnancy. More than half of pregnancy losses were related with abnormal karyotypes, especially aneuploidy. However, due to the high cost of aneuploidy screening, American College of Medical Genetics (ACMG) recommends performing aneuploidy testing on recurrent miscarriage for the third and later pregnancy losses (Levy and Wapner 2018; Sahoo et al. 2017). Most of the first pregnancy losses were not subjected to aneuploidy testing due to the high out-of-pocket cost.

Currently aneuploidy screening on POC from miscarriage can be performed using cytogenetics, FISH, microarray and next-generation sequencing (NGS) methods, all of which have drawbacks. Cytogenetics relies on viable cell culture from recovered from POC. POC has lower success rate in cell culture due to the potential delay in retrieving POC. It also takes days to culture cells and perform G-banding by a certified cytogenetic specialist. FISH assay has a next-day turnaround time, and it's frequently used as an initial screening assay (Fragouli et al. 2011). The cost of FISH though can be greater than $1,200 and require a secondary screening to confirm results. Chromosomal Microarray Analysis (CMA) is currently a first-tier testing for prenatal diagnostics due to its high detection sensitivity (greater than 90%) to chromosomal imbalanced Levy and Wapner 2018; Sahoo et al. 2017). However, it takes 1-2 weeks to obtain CMA results.

The improved methods disclosed herein were used to evaluate tissue from products of conception (POC) samples. In 2 hours, a total of 1.61-1.73M reads were obtained. During the validation, accurate aneuploidy screening results were produced, and caught misinterpreted results from past routine screening. The detection sensitivity of aneuploidy using the improved method for nanopore sequencing was 17/17 (100%) and the detection specificity is 16/16 (100%) at gDNA level. The high detection sensitivity and specificity, fast specimen-to-result time, low assay cost and low setup cost makes it an ideal cost-effective alternative option for aneuploidy screening for pregnancy loss, for a clear definition of lost.

Cancer

The current workflow of NGS targeted cancer panel screening was assessed. A standard Illumina AmpliSeq Cancer Panel Hotspot v2 includes 5-7 hours for library preparation, 17-32 hours for sequencing, and additional data analysis time along with the requirement of an overnight process for gDNA extraction from FFPE tissue. The reported DNA-to-Data Time is 2.5 days. The methods disclosed herein for DNA extraction as well as library preparation, sequencing and data analysis can be shortened to about 2 to 4 hours.

The terms "cancer", "tumor", "cancerous", and "malignant" refer to or describe the physiological condition in mammals that is typically characterized by unregulated cell growth. Examples of cancer include but are not limited to, carcinoma including adenocarcinoma, lymphoma, blastoma, melanoma, sarcoma, and leukemia. More particular examples of such cancers include melanoma, lung cancer, head and neck cancer, renal cell cancer, colon cancer, colorectal cancer, squamous cell cancer, small-cell lung cancer, non-small cell lung cancer, gastrointestinal cancer, Hodgkin's and non-Hodgkin's lymphoma, pancreatic cancer, glioblastoma, glioma, cervical cancer, ovarian cancer, liver cancer such as hepatic carcinoma and hepatoma, bladder cancer, breast cancer, endometrial carcinoma, myeloma (such as multiple myeloma), salivary gland carcinoma, kidney cancer such as renal cell carcinoma and Wilms' tumors, basal cell carcinoma, prostate cancer, vulval cancer, thyroid cancer, testicular cancer, and esophageal cancer.

Examples

The present invention may be better understood by reference to the following non-limiting examples, which are presented in order to more fully illustrate the preferred embodiments of the invention. They should in no way be construed to limit the broad scope of the invention.

Example 1—Method for Rapid DNA Extraction from Mammalian Tissue Materials and Methods Genomic DNA was extracted from approximately 2 mg samples of chorionic villi. Tissues were weighed in an analytical scale (Mettler, AE 100) and placed in a ZR BashingBead Lysis Tubes (2.0 mm) (Zymo, D6015), and mixed with 550 µL BashingBead Buffer (Zymo, D6015) (containing edetate disodium, dihydrate and trometamol) and 10 µL RNase A 20 mg/mL (Invitrogen, 12091021). Each sample was vortexed on a vortex mixer (Fisher, 02-215-422) at maximum speed (3000 rpm) for 7 minutes. Should faster treatment be needed, a high-speed cell disrupter such as FastPrep-24 (max 4750 rpm) or BeadRuptor 24 (max 5000 rpm) can be used to complete the homogenizing process in 3-5 minutes. Each homogenized sample was subjected to centrifugation at 12,000 rcf for 1 minute (Eppendorf centrifuge 5424), and 200 µL supernatant was retrieved for purification. Approximately 0.4 µg DNA per mg tissue was retrieved in this step.

Should additional gDNA be needed for downstream analysis, a 3-minute extension was used with an additional 200 µL Bashing Bead Buffer added to each original ZR BashingBead lysis tube, vortexed for 30 seconds, and the supernatants recovered as above.

Should still more gDNA be needed, needed, another 3-minute extension was used by repeating the additional 200 µL Bashing Bead Buffer incubation step.

Total gDNA yields per sample was the cumulative gDNA recovered from the elutions (FIG. 1). Supernatants were mixed with 3-fold volume of DNA Binding Buffer (Zymo, D4013) at room temperature (approximately 25° C.), and then loaded on a Zymo IC Spin Columns (assembled on a clean 2 mL collection tube) (Zymo, D4013). Spin columns were centrifuged at 10,000 rcf for 30 seconds, and then washed by 500 µL, followed by 200 µL DNA Wash Buffer (Zymo, D4013) at 10,000 rcf for 30 seconds each. The columns containing ultrapure gDNA were then incubated with 40 µL Zymo DNA Elution Buffer (10 mM Tris-HCl, pH 8.5, 0.1 mM EDTA) (Zymo, D4013) at 37° C. for 1-3 minutes, and then centrifuged at 10000 rcf for 30 seconds in a clean low retention 1.5 mL microcentrifuge tube. The quality of gDNA was examined on a 0.8% agarose gel, and the concentration was determined by a Qubit dsDNA HS assay kit (Invitrogen, Q32851).

A comparative study with the Zymo Quick-DNA Tissue/Insect kit (Zymo, D6015) following manufacturer's protocol was performed.

The study was approved by the Columbia University Institutional Review Board.

Results

The Quick-DNA™ Tissue/Insect Microprep Kit (Zymo, D6015) requires the use of β-ME and a fume hood, and multiple columns and purifications steps that increases hands-on time and made automation, which is important for clinical application, challenging.

In the improved method, first β-ME was omitted, however this resulted in poor quality DNA (FIG. 2A). To optimize the purification of gDNA following bead bashing without the need for β-ME, next the manufacturer's purification protocol was compared with a direct DNA Clean & Concentrator-5 (Zymo, D4013) protocol. Compared with the manufacturer's protocol, the direct DNA Clean & Concentrator-5 (Zymo, D4013) protocol had fewer centrifugation steps (5 vs. 7), a shorter centrifugation time (30-sec vs. 1-min), and overall required less time than the kit's protocol (12-min vs. 17.5-min) (FIG. 1). It also only used a single column (IC column vs. III F filter+IC column) and one wash buffer (DNA Wash Buffer vs. DNA Pre-Wash Buffer+g-DNA Wash Buffer). The direct DNA Clean & Concentrator-5 (Zymo, D4013) protocol recovered similar amount of gDNA as the original kit but yielded intact gDNA of larger fragments (>15 kb) instead of smeared DNA (FIG. 2A). Hence, a direct DNA Clean & Concentrator-5 was more suitable to purify gDNA from human soft tissue in combination with 7-8 minute bead-bashing treatment.

The Quick-DNA Tissue/insect kit uses the selective chemistry of different washing buffers to eliminate RNA, but this protocol was insufficient to remove impurity in gDNA from human soft tissues without addition of $\beta$-ME (FIG. 2A). To eliminate these steps, RNase A was added during bead-bashing step so that a simple DNA Clean & Concentrator-5 protocol with one DNA wash buffer was sufficient to yield clean intact gDNA (FIG. 1, FIG. 2A).

Next the 12-minute rapid, and 3- and 6-minute extended bead-bashing based (BBB) gDNA protocols was tested on 34 chronic villi tissue biospecimens (Table 1). gDNA quality was examined by gel electrophoresis (FIG. 2B). Using the 12-minute rapid BBB protocol, 0.40±0.17 μg of gDNA were extracted per mg of tissue (range 0.11 to 0.77 μg per mg of tissue), which is sufficient for downstream applications such as qPCR, MLPA, microarray analysis, and nanopore-based sequencing and similar to gDNA yields using the manufacturer's protocol (1-3 μg gDNA per mg tissue) (FIG. 2D and Table 1).

The 3- and 6-min extended protocols resulted in an additional 0.43±0.23 μg (range 0.08-1.05 μg) and 0.48±0.43 μg (range 0.16-2.45 μg) per mg of tissue, respectively, sufficient yields for whole genome sequencing, genotyping and other downstream analysis (FIG. 2D and Table 1). In total, 0.4-3 μg gDNA were extracted per mg of tissue samples using rapid BBB methods with the 6-min extensions, comparable to commercial kits such as QIAamp DNA Mini Kit (Qiagen, 51304, 0.2-3 μg per mg of tissue) and PureLink gDNA kit (Invitrogen, K182001, 0.4-4 μg per mg tissue).

Finally, the effect of the bead-bashing time on the integrity of large gDNA fragments in lieu of multi-hour lysis steps was investigated. gDNA (100 ng) in TE buffer was subjected to bead-bashing at 3000 rpm for 3, 5, and 10 minutes, and examined a 0.8% agarose gel that confirmed that 10 minutes of the bead-bashing process did not result in an increased amount of sheared DNA (FIG. 2C).

TABLE 1 gDNA yield using rapid, 30-sec extend, and 3-min extend BBB methods.

| Sample | Weight (mg) | 12 min (ng) | 12 min & +3 min Ext. (ng) | Total (ng) | 12 min unit (ng/mg tissue) | 12 min & +3 min Ext. unit (ng/mg tissue) | Total unit (ng/mg tissue) |
|---|---|---|---|---|---|---|---|
| 1 | 3.2 | 1360.0 | 2408.0 | 3584.0 | 425.0 | 752.5 | 1120.0 |
| 2 | 2.0 | 1432.0 | 2488.0 | 3432.0 | 716.0 | 1244.0 | 1716.0 |
| 3 | 2.0 | 680.0 | 1272.0 | 1832.0 | 340.0 | 636.0 | 916.0 |
| 4 | 4.1 | 1640.0 | 3000.0 | 4240.0 | 400.0 | 731.7 | 1034.1 |

TABLE 1-continued gDNA yield using rapid, 30-sec extend, and 3-min extend BBB methods.

| Sample | Weight (mg) | 12 min (ng) | 12 min & +3 min Ext. (ng) | Total (ng) | 12 min unit (ng/mg tissue) | 12 min & +3 min Ext. unit (ng/mg tissue) | Total unit (ng/mg tissue) |
|---|---|---|---|---|---|---|---|
| 5 | 2.1 | 872.0 | 1604.0 | 2216.0 | 415.2 | 763.8 | 1055.2 |
| 6 | 3.0 | 1440.0 | 2648.0 | 3752.0 | 480.0 | 882.7 | 1250.7 |
| 7 | 1.9 | 856.0 | 1504.0 | 2148.0 | 450.5 | 791.6 | 1130.5 |
| 8 | 2.2 | 584.0 | 1068.0 | 1584.0 | 265.5 | 485.5 | 720.0 |
| 9 | 2.5 | 1008.0 | 1808.0 | 2476.0 | 403.2 | 723.2 | 990.4 |
| 10 | 2.2 | 832.0 | 1720.0 | 2396.0 | 378.2 | 781.8 | 1089.1 |
| 11 | 2.0 | 1536.0 | 2832.0 | 3360.0 | 768.0 | 1416.0 | 1680.0 |
| 12 | 2.3 | 576.0 | 1056.0 | 1456.0 | 250.4 | 459.1 | 633.0 |
| 13 | 0.9 | 584.0 | 1308.0 | 1960.0 | 648.9 | 1453.3 | 2177.8 |
| 14 | 1.3 | 920.0 | 1912.0 | 2257.6 | 707.7 | 1470.8 | 1736.6 |
| 15 | 0.4 | 272.0 | 524.0 | 610.0 | 680.0 | 1310.0 | 1525.0 |
| 16 | 4.3 | 1984.0 | 4640.0 | 5792.0 | 461.4 | 1079.1 | 1347.0 |
| 17 | 1.1 | 310.4 | 556.8 | 1892.0 | 282.2 | 506.2 | 1720.0 |
| 18 | 1.8 | 456.0 | 976.0 | 3122.0 | 253.3 | 542.2 | 1734.4 |
| 19 | 1.1 | 278.4 | 508.8 | 1106.0 | 253.1 | 462.5 | 1005.5 |
| 20 | 4.7 | 1360.0 | 2760.0 | 6032.0 | 289.4 | 587.2 | 1283.4 |
| 21 | 0.5 | 208.0 | 406.4 | 675.6 | 416.0 | 812.8 | 1351.2 |
| 22 | 2.4 | 1024.0 | 2000.0 | 3784.0 | 426.7 | 833.3 | 1576.7 |
| 23 | 3.3 | 488.0 | 866.0 | 1980.0 | 147.9 | 262.4 | 600.0 |
| 24 | 1.3 | 283.2 | 597.2 | 1462.8 | 217.8 | 459.4 | 1125.2 |
| 25 | 0.7 | 172.0 | 378.0 | 2096.0 | 245.7 | 540.0 | 2994.3 |
| 26 | 2.3 | 247.2 | 435.6 | 1023.6 | 107.5 | 189.4 | 445.0 |
| 27 | 2.4 | 668.0 | 3196.0 | 4156.0 | 278.3 | 1331.7 | 1731.7 |
| 29 | 1.1 | 500.0 | 1168.0 | 1588.0 | 454.5 | 1061.8 | 1443.6 |
| 30 | 1.1 | 412.0 | 1020.0 | 1340.0 | 374.5 | 927.3 | 1218.2 |
| 31 | 5.5 | 1232.0 | 3176.0 | 4136.0 | 224.0 | 577.5 | 752.0 |
| 32 | 1.3 | 596.0 | 1532.0 | 2040.0 | 458.5 | 1178.5 | 1569.2 |
| 33 | 4.6 | 2120.0 | 4648.0 | 5976.0 | 460.9 | 1010.4 | 1299.1 |
| 34 | 3.2 | 460.0 | 1252.0 | 1752.0 | 143.8 | 391.3 | 547.5 |

Example 2—Rapid Direct Ligation Nanopore Short-Read Library Preparation Materials Quick-DNA Tissue/Insect kit (Zymo, D6015)
DNA Clean & Concentrator-5 (Zymo, D4013)
Select-a-Size DNA Clean & Concentrator Kit (Zymo, D4080)
Covaris microTUBE (Covaris, 520045)
Ultra II End Repair/dA-tailing module (NEB, E7546)
Blunt/TA Ligase Master Mix (NEB, M0367)
Barcodes 01-12
Proof 200 absolute ethanol
EDTA (Invitrogen, AM9260G)
MgCl$_2$ (Invitrogen, AM9530G)
100 mM ATP (Thermo Fisher, R1441)
Buffer EB (Qiagen, 1014609)
Nuclease-free water (Invitrogen, AM9937)
1 μM AMII adaptor (Oxford Nanopore, EXP-NBD104)
Qubit dsDNA HS assay kit (Invitrogen, Q32851)

Methods

1) Fragmentation

Loaded 25 μL gDNA in a microTUBE, subjected to Covaris fragmentation using manufacturer's 500 bp setting.

2) End Preparation

Prepared Ultra II end repair master mix by mixing 21 μL Ultra II End repair buffer and 9 μL Ultra II End repair enzyme mix.

In a PCR strip, assembled an Ultra II End repaired/dA-tailing reaction in a well for each sample:

| 500 bp DNA~5ng/μL | 10μL |
| Ultra II End repair master mix | 2μL |
| Total | 12μL |

The reaction was subjected to an end-preparing program on a thermocycler:
20° C. for 5 minutes;
65° C. for 7 minutes; and
4° C. hold

3) Ligation

In each end prepared reaction, added the following reagents:
0.5 μL barcode (see Tables 2 and 9)
12.5 μL Blunt/TA Ligase Master Mix The reaction was subjected to a 10-minute room temperature (25° C.) incubation in a thermocycler.

Prepared SAS400 mix by mixing 500 μL Select-A-Size binding buffer and 5 μL absolute ethanol, scaled up.

In each ligation reaction, 2 μL 250 mM EDTA and 136.4 μL SAS400 mix were added to stop the ligation reaction. All the reactions were combined in a 5 mL Eppendorf tube, and gently mixed.

The combined reactions were purified using a Zymo IC-S column (Zymo, D4080, orange) following manufacturer's protocol, but washed using 400 μL-200 μL-200 μL-200 μL SAS400 mix for 10 second 13,000 rpm spin each before the normal washes using DNA wash buffer.

Eluted DNA using 11.5 μL 1/5 Buffer EB (2 mM Tris-HCl, pH 8.5). Used 1 μL for Qubit dsDNA HS assay to determine the concentration of recovered DNA.

4) Final Ligation

In a clean PCR tube, assembled the following reaction:

| DNA | 0.44 | pmol |
| 1 μM AMII | 0.65 | μL |
| 1/5 Buffer EB | up to 5 | μL |
| Enhancer mix | 0.60 | μL |
| Blunt/TA Ligase | 0.25 | μL |
| Total | 5.85 | μL |

RT incubation for 10 minutes. This can be done while priming the MinION flowcell.

5 μL (approximately 0.4 pmol) ligation product for sequencing, 0.3 μL ligation product for quality check on 3% agarose gel (FIG. 3). As shown in the representative gel in FIG. 4, after final ligation the barcoded DNA was ligated to the nanopore sequencing adaptor sufficiently, causing a significant shift in Lane 2. There was no visible unligated nanopore sequencing adaptor in the final library as shown in Lane 2.

If the recovered barcoded DNA was less than 35 ng/μL, the ligation can be scaled by adding 0.12-fold volume of DNA plus AMII adapter. Use 0.25 μL Blunt/TA ligase master mix.

The efficiency was tested for up to 12 μL.

Loaded approximately 0.4 pmol final library for sequencing.

TABLE 2

V-barcode sequences for Examples 3-5

| Barcode ID | Sequence | Tm (° C.) |
|---|---|---|
| V01 | CGTTGCAGCGATGCTAGATGTGTATAAGAGACAG (SEQ ID NO: 1) | 62.4 |
| V02 | CGAAGGATTGAGCAGAGATGTGTATAAGAGACAG (SEQ ID NO: 2) | 60.6 |
| V03 | CATCATCGTGTCATTAGATGTGTATAAGAGACAG (SEQ ID NO: 3) | 58 |
| V04 | CGAAGATGCGACGTTAGATGTGTATAAGAGACAG (SEQ ID NO: 4) | 60.7 |
| V05 | CTGCCAGAAGACCTCAGATGTGTATAAGAGACAG (SEQ ID NO: 5) | 61.7 |
| V07 | CGATCGTCGGATGAAAGATGTGTATAAGAGACAG (SEQ ID NO: 6) | 60.6 |
| V08 | CGTTAATGCGACAGAAGATGTGTATAAGAGACAG (SEQ ID NO: 7) | 59.7 |
| V09 | CTTCCGATCGTTACCAGATGTGTATAAGAGACAG (SEQ ID NO: 8) | 60.4 |
| V10 | CGACGCTCTGTTCATAGATGTGTATAAGAGACAG (SEQ ID NO: 9) | 60.4 |
| V11 | CCTCAAATCGGATGTAGATGTGTATAAGAGACAG (SEQ ID NO: 10) | 59.1 |
| V12 | CATTGATCGGACGCAAGATGTGTATAAGAGACAG (SEQ ID NO: 11) | 61.1 |
| V13 | CGATATCCGGCAACGAGATGTGTATAAGAGACAG (SEQ ID NO: 12) | 61.9 |

Example 3—Aneuploidy Screening of CVS Samples

Materials and Methods

Overall Study Design

Figure 4A:
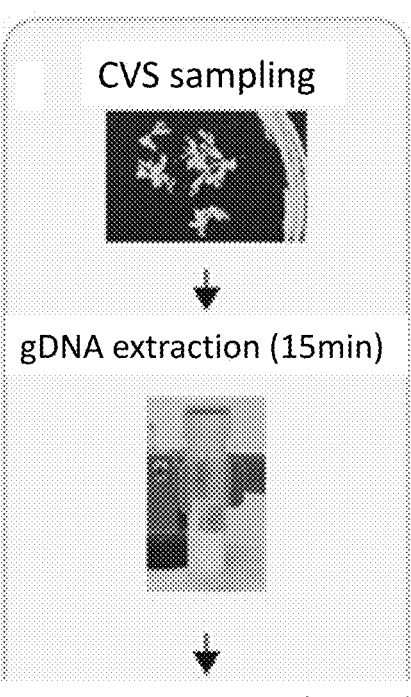
FIG. 4A is a schematic overview of the workflow of rapid nanopore aneuploidy screening for CVS samples.
Figure 4A:
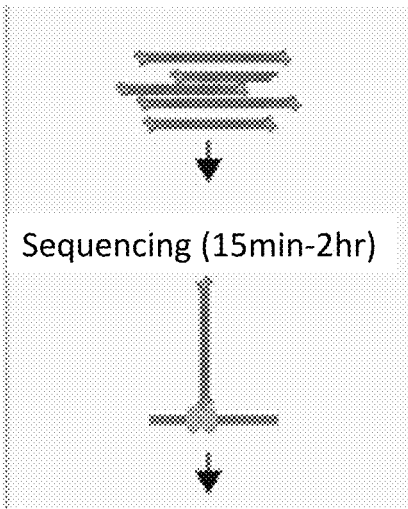
Figure 4A:
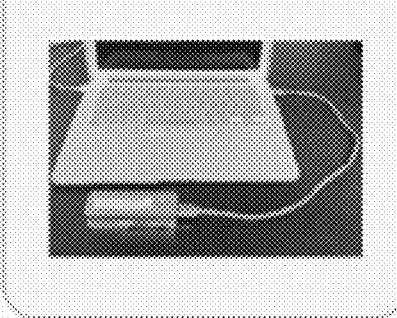

Aneuploidy screening results from CVS samples using same-day, whole-genome, nanopore-based sequencing and conventional G-banding karyotyping was compared. The overall workflow is shown in FIG. 4A. The study was approved by the Institutional Review Board of Columbia University Irving Medical Center (IRB-AAAR4986).

Sample Preparation

Genomic DNA (gDNA) was extracted from blinded, excess, villus tissues (approximately 2 mg) obtained from clinically indicated chorionic villus sampling (CVS), as well as a known male CVS sample and from a normal male B-lymphocyte cell line (GM12877, Coriell Institute) using the Zymo Quick-DNA Tissue/Insect Microprep kit (Zymo, D6015) and the method of Example 1. For each sample, 25 μL gDNA was processed in a Covaris microTUBE (Covaris, 520045) using manufacturer's setting for 500 bp fragments. Approximately 50 ng fragmented gDNA were subjected Ultra II End Repair/dA-tailing module (NEB, E7546) as reported previously (Wei, Williams and Weiss 2018; Wei et al. 2018b). An optimized approximately 45 minute short-read nanopore library preparation was used as described in Example 2, with in-house synthesized barcodes and re-concentrated adapters to reduce technical variations and batch effects (Wei and Williams 2016; Wei, Williams and Weiss 2018).

Sequencing

Barcoded samples, consisting of blinded euploid and aneuploid specimens and one male reference sample were tested using nanopore sequencing on the MinION R9.4.1 flowcell (Oxford Nanopore, FLO-MIN106.Rev.D) on MinIT v19.05.2 using a fast basecalling mode of LSK109 script. Sequencing run were set for 3 hours and sequencing data from the first 2 hours were collected and used for data analysis.

Data Analysis

Data analysis was performed using a custom analysis pipeline as described previously (Wei, Williams and Weiss 2018; Wei and Williams 2016). Fastq format of sequences generated in 2 hours and that passed the basecaller quality filter were first converted to fasta format and subjected cutadapt v1.14. for demultiplexing based on the in-house barcodes as reported (Wei, Williams and Weiss 2018). Demultiplexed sequences were aligned to human reference genome Hg19 using parallel blat pBlat (http://icebert.github.io/pblat/) (Wei, Williams and Weiss 2018; Wei and Williams 2016). Uniquely aligned reads on each chromosome were summarized and normalized and used to estimate the relative copy number of each chromosome using the adjusted Z-Score method reported previously (Wei, Williams and Weiss 2018; Wei et al. 2018b). Parallel blat alignment using on a 96-core CPU required approximately 30 minutes and less than 10 minute for demultiplexing (Wei and Williams 2016; Wei et al. 2018a; Wei, Weiss and Williams 2018). Minimap2 was evaluated as a fast aligner during development but generated higher false possible detection than parallel BLAT.

For detection of large CNV (≥20 Mb) and full aneuploidy, a minimum of 80K reads were used. Use of a minimum of 80K reads reduced the coefficient of variation (CV) of reads assigned to each bin by approximately 30% on average compared with using 60K reads (Table 3). Using a virtual reference based on a census on multiple normal male samples from preliminary study further reduced the CV of reads assigned to each bin by approximately 45% on average compared with using a known normal sample (Table 3). Large CNVs were detected by segregating human reference genome into 10 Mbs bins, and aneuploidy detection was performed for each bin as described above. Bins with fewer than 80 uniquely assigned (UA) reads in the normal male reference were eliminated from large CNV detection assay. Bins with ≥200 UA reads in the reference sample, bins with a Z-score >3.29 were considered as a gain in CNV, while bins with a Z-score <−3.29 was considered as a loss in CNV (P=0.001). For bins with 161-200 UA reads in the normal male reference sample, bins with Z-score >4 were considered as gain in CNV, and bins with Z-score <4 were considered as loss in CNV (P<0.0001). For bins with 141-160 UA reads in the normal male reference sample, bins with Z-score >5 were considered as gain in CNV, and bins with Z-score <5 were considered as loss in CNV (P<0.00001). For bins with 80-140 UA reads in the normal male reference sample, bins with Z-score >6 were considered as gain in CNV, and bins with Z-score <6 were considered as loss in CNV (P<0.000001). Two bins with |Z-score|>3.29 were concatenated. Large CNVs≥20 Mbs were reported.

Results

Technical Evaluation Using Control DNA

Figure 4C:
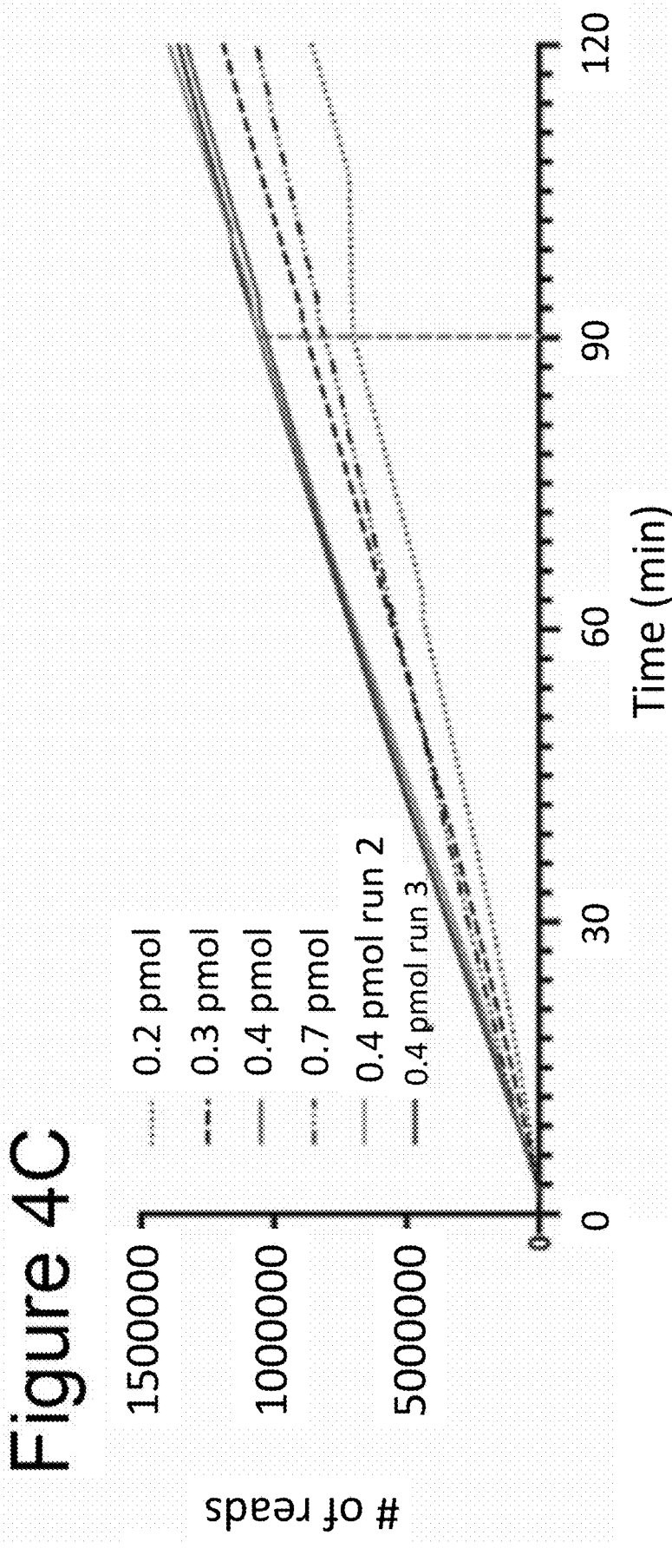
FIG. 4C is a graph showing the results of a titration experiment of library input and the effects on sequencing yield. The conditions for optimization (0.2 pmol, 0.3 pmol, 0.7 pmol) are shown in dotted or darted black; the optimized condition (approximately 0.4 pmol) as determined by a quadratic regression was showed in solid lines in different colors, indicating different sequencing runs.

For technical evaluation of the rapid direct-ligation method for DNA library preparation, genomic DNA (gDNA) from a normal B-lymphocyte cell line (Coriell Institute, NA12877) was were subjected to twelve barcodes (i.e. 12 technical repeats) using the rapid direct-ligation method to prepare a short-read nanopore sequencing library described in Example 2. Libraries of 0.2 pmol, 0.3 pmol, and 0.7 pmol were subjected to individual nanopore runs, and sequencing yields were monitored (FIG. 4C). At 1.5 hours, 701K, 876K, and 809K reads passed the sequence quality filter, respectively. Predicted by a quadratic regression (y=−3835x²+3667.5x+120.9), the best sequencing performance should be approximately 0.4 pmol with a peak sequencing yield of approximately 998K high quality reads, and thus approximately 0.4 pmol library input was used for sequencing actual CVS samples. In fine sequencing runs with actual CVS samples, 1,029K to 1,388K reads passed the sequence quality filter at 1.5 hours, counting for 46.7%-98.0% increase in sequencing yield than using the recommended library input.

Rapid Detection of Aneuploidy on Tissues from CVS

Having demonstrated the optimal short-read library input with the reference control sample, blinded CVS samples (n=52) and a known normal male reference sample were sequenced in batches of 10 blinded CVS test samples and a reference normal male CVS sample, across five nanopore sequencing runs (Table 3).

Figure 4D:
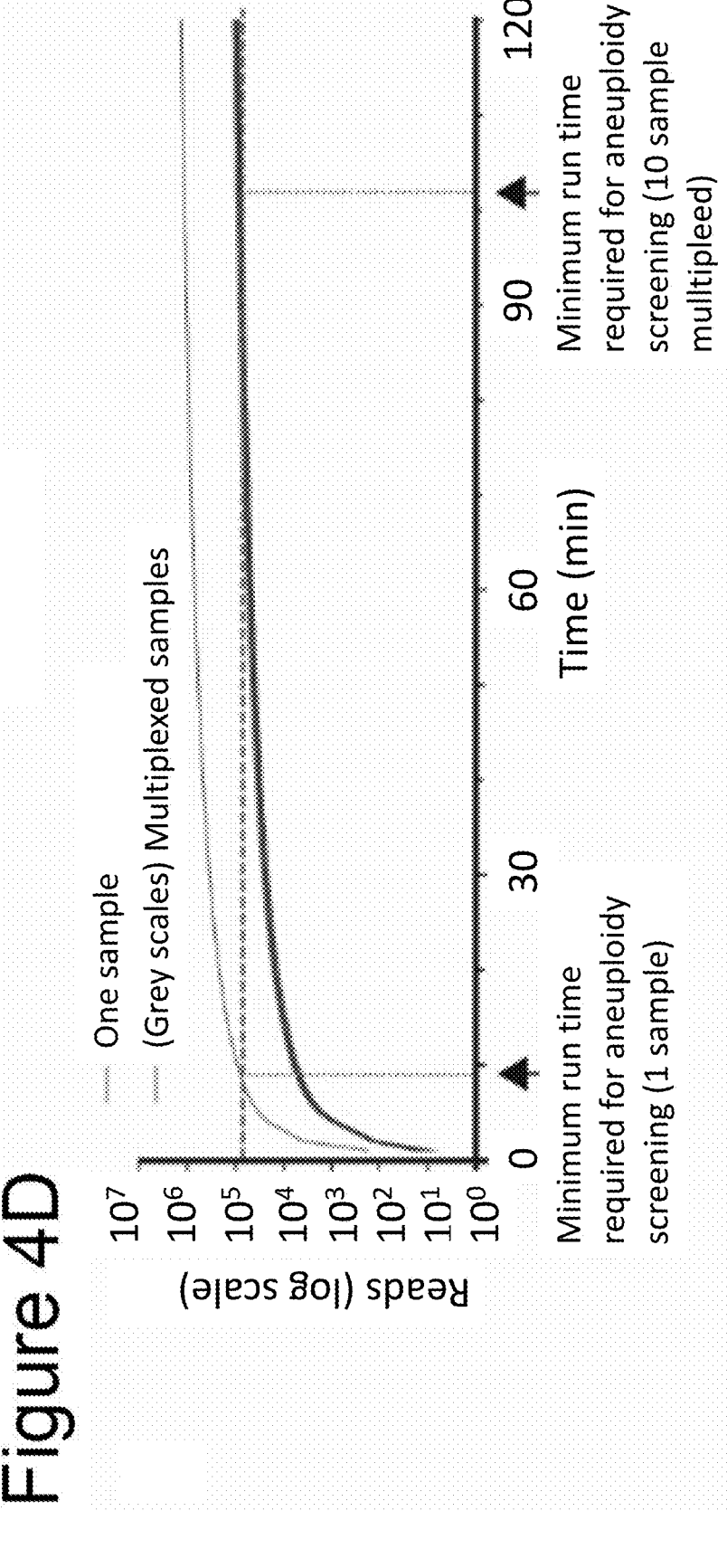
FIG. 4D shows the results of an example run of yield of 12 samples within 1 sequencing run. Samples 1-12 are shown in different scale of dark gray curves, the total sequencing yield shown in light gray curve (top curve), and the threshold yield sufficient to performed aneuploidy screening shown in the dotted straight line.

The sequencing rate was 13,413-17,044 reads/min (FIG. 4D). In the first 10 minutes, 96,276-132,317 reads were generated, of which 86,857-126,255 reads were of high quality, sufficient to perform accurate aneuploidy screening of a single sample (Wei, Williams and Weiss 2018; Wei and Williams 2016). In 2 hours, a total of 1.61-2.05M reads were obtained, comprising 1.33-1.82M high quality reads. Multiplexing twelve samples on a single sequencing run yielded 82,144-161,027 high quality reads generated from each sample, sufficient for detecting aneuploidy (Table 3). The barcodes performed uniformly with the Coefficient of Variation (CV) of reads assigned to each barcode within a run ranging from 4.77% to 12.67%, compared to 38.4% using the manufacturer's kit barcodes.

Figure 5:
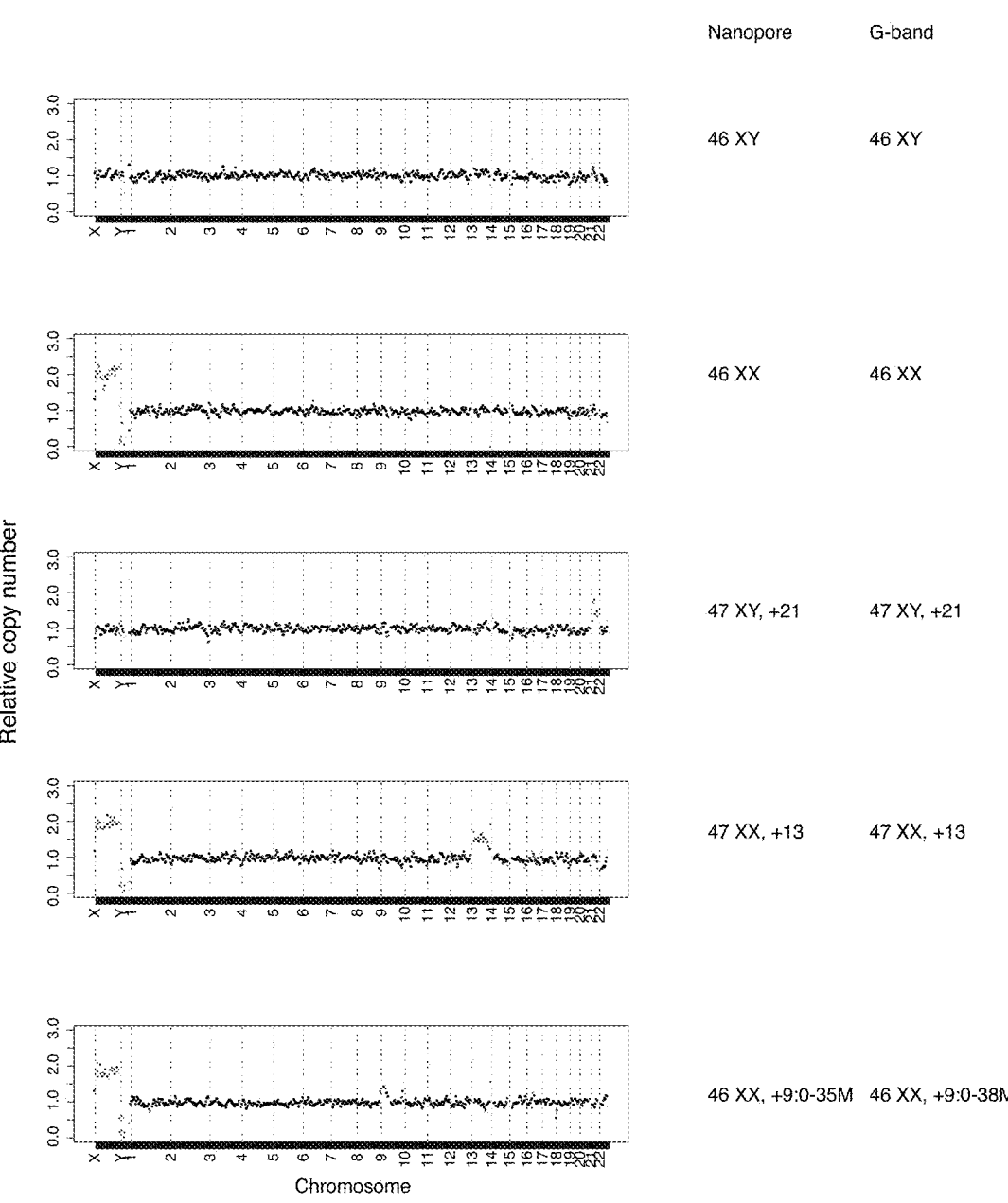
FIG. 5 are sample dotplots of CVS samples with 1 normal and 1 aneuploidy, and 1 large CNV.

After results were determined for the blinded samples, samples were unblinded. There was 100% concordance with the G-banding karyotype results among the 42 euploid, 7 trisomic, 2 mosaic trisomy, and 1 large CNV (~38 Mb) (FIG. 5, Tables 4 and 5). The detection sensitivity and specificity were both 100% (Table 5). The amount of time required from tissue to results was 2-4 hours for the nanopore-based aneuploidy screening, depending on the number of samples multiplexed (FIG. 4D). The cost of reagents for conducting the assay was $32.50 (USD) per sample when multiplexed samples were used.

Figure 6:
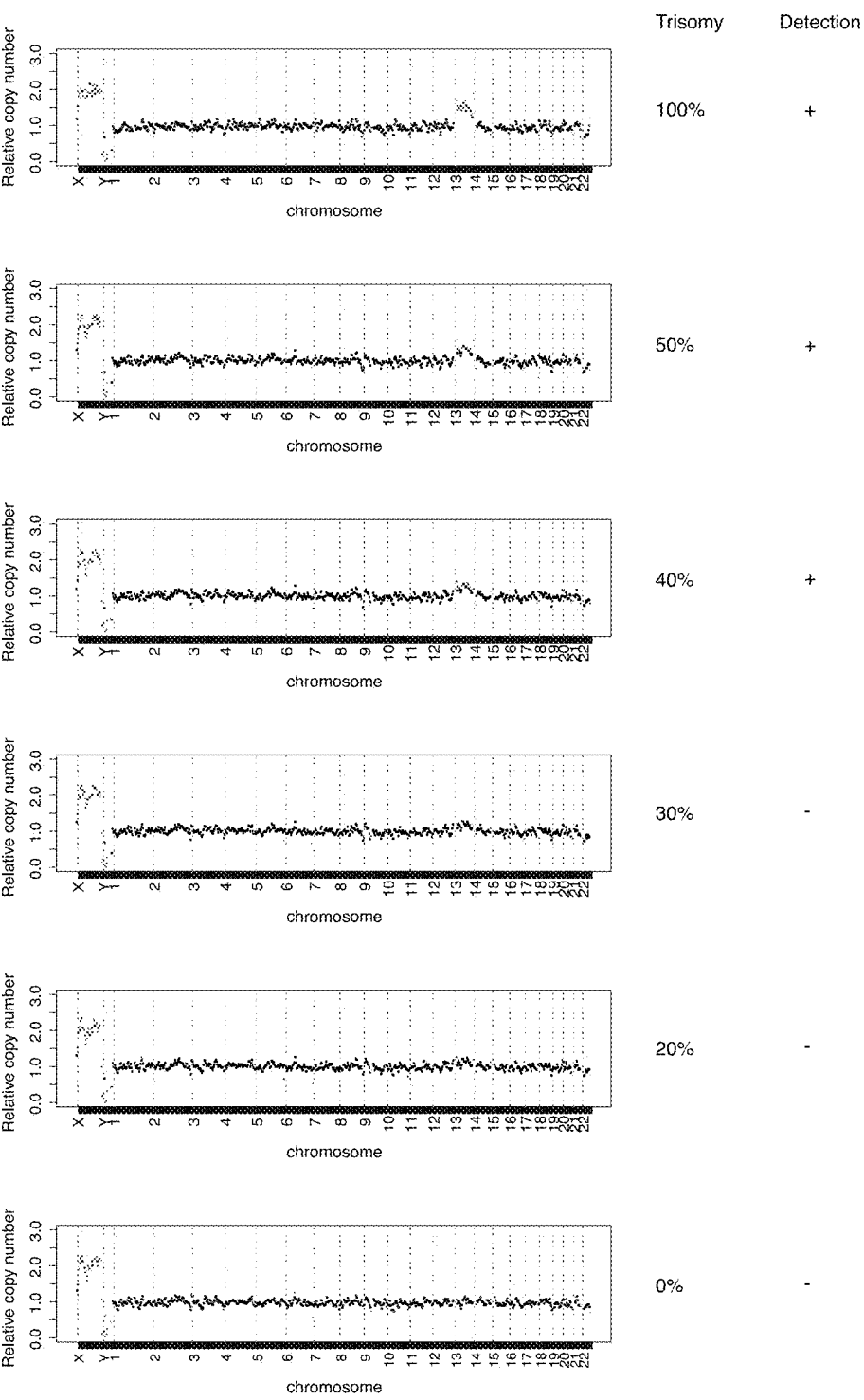
FIG. 6 are dotplots of a simulated titration experiment of trisomy contents. A trisomy 13 was mixed with normal samples of the same sex at 50%, 40%, 30%, and 20% to determine the theoretical detection limit of the data analysis pipeline.

To evaluate detection of aneuploidy mosaicism, a dataset using mixed reads from a normal sample and a trisomy sample with mosaicism rates of 20%, 30%, 40% and 50% was used. Chromosomes with ≥20% copy number changes (approximately 40% mosaicism) compared to a normal male reference were detected with high confidence across the chromosome (FIG. 6). This is considered as the theoretical lower detection limit with high confident using the current method.

TABLE 3

| | | | | | Nanopore Aneuploidy Screening Results | | |
| | | | | | Nanopore Aneuploidy screening | | |
| | Sample | ID | Barcode | Sex | Aneuploidy | Comment | G-band karyotype |
|---|---|---|---|---|---|---|---|
| Run1 | 1 | LL17-0014 | V01 | XX | +21 | | 47 XX, +21 |
| | 2 | LL17-0018 | V02 | XY | +21 | | 47 XY, +21 |
| | 3 | LL17-0012 | V03 | XY | | | 46 XY |
| | 4 | LL17-0013 | V04 | XY | | | 46 XY |
| | 5 | LL17-0021 | V05 | XY | | | 46 XY |
| | 6 | LL17-0030 | V07 | XX | | | 46 XX |
| | 7 | LL18-0001 | V08 | XY | | | 46 XY |
| | 8 | LL18-0003 | V09 | XY | | | 46 XY |
| | 9 | LL18-0030 | V10 | XX | +13 | | 47 XX, +13 |
| | 10 | LL18-0017 | V11 | XY | | | 46 XY |
| | 11 | LL18-0016 | V12 | XY | | Reference | 46 XY |
| | 12 | LL17-0029 | V13 | XX | +21 | | 47 XX, +21 |
| Run2 | 1 | LL17-0022 | V01 | XX | | | 46 XX |
| | 2 | LL17-0023 | V02 | XY | | | 46 XY |
| | 3 | LL17-0024 | V03 | XX | | | 46 XX |
| | 4 | LL17-0025 | V04 | XY | | | 46 XY |
| | 5 | LL17-0026 | V05 | XX | | | 46 XX |
| | 6 | LL17-0027 | V07 | XY | | | 46 XY |
| | 7 | LL18-0024 | V08 | XY | | | 46 XY |
| | 8 | LL18-0025 | V09 | XY | | | 46 XY |
| | 9 | LL18-0028 | V10 | XY | | | 46 XY |
| | 10 | LL18-0029 | V11 | XX | | | 46 XX |
| | 11 | LL18-0016 | V12 | XY | | Reference | 46 XY |
| Run3 | 1 | LL18-0010 | V01 | XY | | | 46 XY |
| | 2 | LL18-0011 | V02 | XX | +9:0-35M | Translocation, large CNV | 46 XX, 38M unbalanced translocation on chr9 |
| | 3 | LL18-0012 | V03 | XX | | | 46 XX |
| | 4 | LL18-0013 | V04 | XY | | | 46 XY |
| | 5 | LL18-0014 | V05 | XY | | | 46 XY |
| | 6 | LL18-0015 | V07 | XX | | | 46 XX |
| | 7 | LL18-0019 | V08 | XX | | | 46 XX |
| | 8 | LL18-0020 | V09 | XX | | | 46 XX |
| | 9 | LL18-0022 | V10 | XY | | | 46 XY |
| | 10 | LL18-0023 | V11 | XY | | | 46 XY |
| | 11 | LL18-0016 | V12 | XY | | Reference | 46 XY |
| Run4 | 1 | LL18-0037 | V01 | XX | not full +18 | Inconclusive: possible risk of mosaic T18, or T18 with MCC | Mosaic +18, a twin, 7% MCC |
| | 2 | LL18-0038 | V02 | XX | | | 46 XX |
| | 3 | LL18-0042 | V03 | XY | +18 | | 47 XY, +18. 35% MCC |
| | 4 | LL18-0043 | V04 | XX | +18 | | 47 XX, +18 |
| | 5 | LL17-0010 | V05 | XX | | | 46 XX |
| | 6 | LL17-0011 | V07 | XX | | | 46 XX |
| | 7 | LL17-0020 | V08 | XY | | | 46 XY |
| | 8 | LL17-0028 | V09 | XY | | | 46 XY |
| | 9 | LL18-0046 | V10 | XY | +21 | | 47 XY, +21 |
| | 10 | LL18-0048 | V11 | XY | | | 46 XY |
| | 11 | CVS-male | V12 | XY | | Reference | 46 XY |
| Run5 | 1 | LL18-0049 | V01 | XY | | | 46, XY |
| | 2 | LL19-0001 | V02 | XY | | | 46, XY |
| | 3 | LL19-0004 | V03 | XY | | Noisy | 46, XY |
| | 4 | LL19-0006 | V04 | XY | | | 46, XY |
| | 5 | LL19-0010 | V05 | XX | | | 46, XX |
| | 6 | LL19-0011 | V07 | XY | | Noisy | 46, XY |
| | 7 | LL19-0012 | V08 | XY | +18 | | 47, XY, +18 |
| | 8 | LL19-0014 | V09 | XY | | | 46, XY |
| | 9 | LL18-0022 | V10 | XY | | | 46, XY |
| | 10 | LL18-0023 | V11 | XY | | | 46, XY |
| | 11 | LL18-0016 | V12 | XY | | | 46, XY |
| | 12 | CVS-male | V13 | XY | | Reference | 46, XY |

27

TABLE 4

Comparison of CV on autosomal relative copy number of CVS Samples in Run 1

| Sam-ple | 60K-V12R | 80K-V12R | 80K-VR | 100K-VR | 80K vs. 60K (%) | VR vs. V12R (%) | 100K vs. 80K (%) |
|---|---|---|---|---|---|---|---|
| 1 | 0.2373 | 0.1706 | 0.1035 | 0.0997 | −28.1 | −39.3 | −3.7 |
| 2 | 0.3699 | 0.2411 | 0.1168 | 0.1133 | −34.8 | −51.5 | −3.0 |
| 3 | 0.2637 | 0.1895 | 0.1078 | 0.0997 | −28.1 | −43.1 | −7.6 |
| 4 | 0.3105 | 0.1590 | 0.0988 | 0.0957 | −48.8 | −37.9 | −3.1 |
| 5 | 0.1471 | 0.1451 | 0.0922 | 0.0832 | −1.4 | −36.5 | −9.7 |
| 6 | 0.2687 | 0.1680 | 0.0896 | 0.0800 | −37.4 | −46.7 | −10.7 |
| 7 | 0.2744 | 0.1841 | 0.0719 | 0.0695 | −32.9 | −60.9 | −3.4 |
| 8 | 0.1482 | 0.1621 | 0.0750 | 0.0699 | 9.4 | −53.7 | −6.9 |
| 9 | 0.2776 | 0.1863 | 0.1419 | 0.1380 | −32.9 | −23.8 | −2.8 |
| 10 | 0.3632 | 0.2138 | 0.0945 | 0.0881 | −41.1 | −55.8 | −6.8 |
| 11 | 0.0000 | 0.0000 | 0.0968 | 0.0782 | N/A | N/A | −19.3 |
| 12 | 0.2726 | 0.2002 | 0.1157 | 0.1113 | −26.6 | −42.2 | −3.7 |

TABLE 5

Summary of nanopore aneuploidy screening results

| | Result |
|---|---|
| Sample size (n) | 52 |
| Sensitivity for aneuploidy, large CNV, and mosaic (%) | 100 (10/10) |
| Specificity for aneuploidy, large CNV, and mosaic (%) | 100 (42/42) |
| PPV (%) | 100 (10/10) |
| NPV (%) | 100 (42/42) |

Example 4—Aneuploidy Screening of Embryo Samples

Materials and Methods

Figure 7:
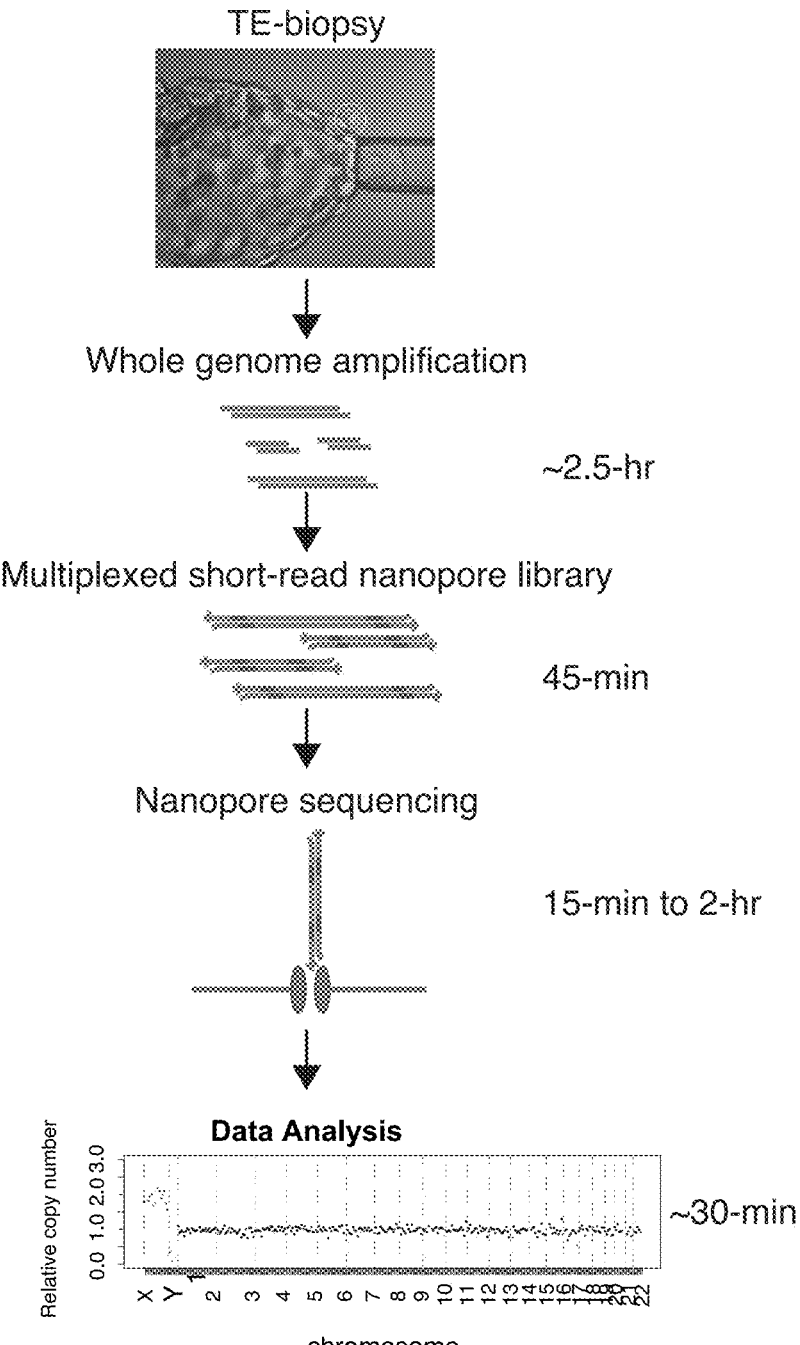
FIG. 7 is a schematic overview of the workflow of rapid nanopore aneuploidy screening for embryo samples.

Aneuploidy screening results from embryo samples using same-day, whole-genome, nanopore-based sequencing and next-generation-sequencing (NGS) preimplantation genetic testing-aneuploidy (PGT-A) was compared. The overall workflow is shown in FIG. 7. The study was approved by the Institutional Review Board of Columbia University Irving Medical Center.

The methods used in Examples 2 through 3 were used. To obtain sufficient DNA for the assay, 3-5 cells were biopsied from an embryo in blastocyst stage using Trophectoderm (TE)-biopsies and subjected to whole genome amplification (PicoPlex/SurePlex). Additionally, the fragmentation step in the methods used in Examples 2 and 3 was not needed for DNA amplified with a PicoPlex/SurePlex Whole Genome Amplification kit.

Results

Figures 8, 8A, 8B, 8C:
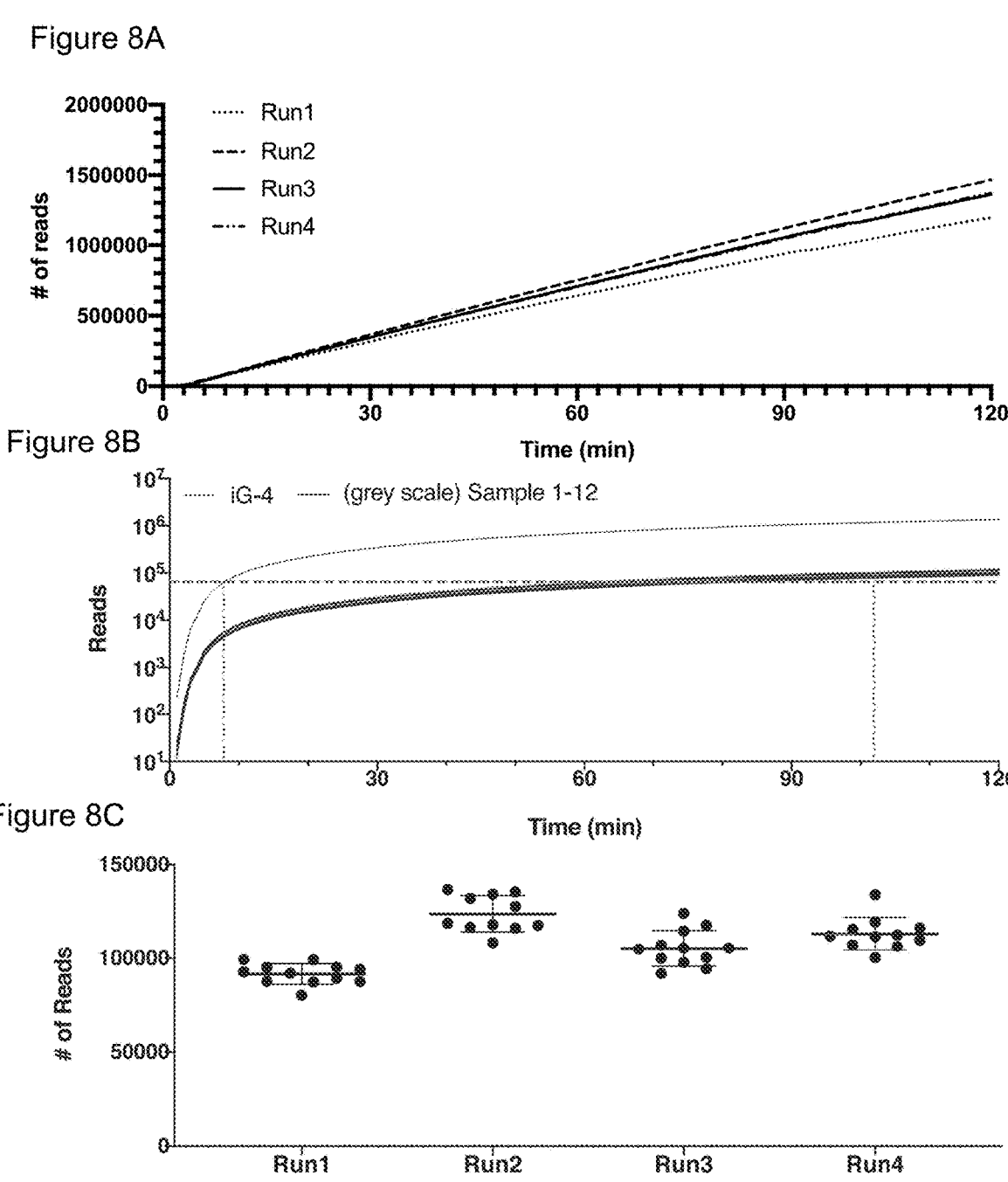
FIG. 8 shows the results of the use of the rapid nanopore sequencing method for aneuploidy screening of embryo samples.
FIG. 8A is a graph showing the results of four runs, the number of reads over time.
FIG. 8B shows the results of an example run of yield of 12 samples within 1 sequencing run. Samples 1-12 are shown in different scale of dark gray curves, the total sequencing yield shown in light gray curve (top curve), and the threshold yield sufficient to performed aneuploidy screening shown in the dotted straight line.
FIG. 8C is a plot showing the comparison of run performance using. The reads assigned to each sample are represented by a dot. The mean and SD are shown by error bars.

In 2 hours, a total of 1.36-1.68M reads were obtained, comprising 1.22-1.50M high quality reads (FIG. 8A). The amount of time required from tissue to results was 2-4 hours for the nanopore-based aneuploidy screening, depending on the number of samples multiplexed (FIG. 8B). After results were determined for the blinded samples, samples were unblinded. There was 100% concordance with the G-banding karyotype results among the 29 euploid and 3 large CNV and about 89% among the full aneuploidy and 50% among the mosaic aneuploidy. The detection specificity was 100% (Tables 6 and 7).

TABLE 6

Summary of Nanopore PGT-A results in comparison with NGS

| Condition | Sam-ple | Detected | False Positive | False Negative | Sensitivity | Speci-ficity |
|---|---|---|---|---|---|---|
| Full aneuploidy | 9 | 8 | 0 | 1 | 88.9% (8/9) | 100% (29/29) |
| Mosaic aneuploidy | 2 | 1 | 0 | 1 | 50% (1/2) | 100% (29/29) |
| Large CNV | 3 | 3 | 1 | 0 | 100% (3/3) | 96.7% (29/30) |
| Euploid | 29 | 29 | 0 | 0 | 100% (29/29) | 100% (29/29) |

TABLE 7

Comparison of PGT-A testing results
Nanopore PGT-A

| Run | ID | sample | Barcode | Sex | Aneuploidy | Comment | NGS PGT-A |
|---|---|---|---|---|---|---|---|
| Run1 | JB-2 | 1 | V01 | XX | | Reference | 46 XX |
| | JB-3 | 2 | V02 | XY | | | 46 XY |
| | JB-4 | 3 | V03 | XY | | | 46 XY |
| | JB-7 | 4 | V04 | XX | | | 46 XX |
| | JB-8 | 5 | V05 | XY | | | 46 XY |
| | JB-9 | 6 | V13 | XX | | | 46 XX |
| | JB-10 | 7 | V07 | XY | +21 | | 47 XY, +21 |
| | JB-11 | 8 | V08 | XY | −2, −19 | | 44 XY, −2, −19 |
| | JB-13 | 9 | V09 | XY | | | 46 XY |
| | JB-14 | 10 | V10 | XY | | | 46 XY |
| | JB-17 | 11 | V11 | XY | | | 46 XY |
| | JB-18 | 12 | V12 | XY | +9, +16 | | 48 XY, +9, +16 |
| Run2 | ER36 | 1 | V01 | XY | | | 46, XY |
| | ER37 | 2 | V02 | XY | | | 46, XY |
| | ER38 | 3 | V03 | XX | | | 46, XX |
| | ER39 | 4 | V04 | XX | | | 46, XX |
| | ER41 | 5 | V05 | XX | +1 | | 47, XX, +1 |
| | ER42 | 6 | V07 | XY | −14 | | 45, XY, −14 |
| | ER43 | 7 | V08 | XY | | | 46, XY |
| | ER44 | 8 | V09 | XX | | | 46, XX |
| | ER45 | 9 | V10 | XY | | | 46, XY |
| | ER46 | 10 | V11 | XY | | | 46, XY |

TABLE 7-continued

Comparison of PGT-A testing results
Nanopore PGT-A

| Run | ID | sample | Barcode | Sex | Aneuploidy | Comment | NGS PGT-A |
|---|---|---|---|---|---|---|---|
| | JB-3 | 11 | V12 | XY | | | 46, XY (ref) |
| | iG-1 male mix | 12 | V13 | XY | | Reference | 46, XY (ref) |
| Run3 | ER13 | 1 | V01 | XY | +10:0-55M | ~0.25-fold mos −1:10M-60M, but full | XY, +10p |
| | ER16 | 2 | V02 | XY | +13, −21, −22 | aneuploidy on 13, 21, 22. This can be a | XY, +13, −21, −22 |
| | ER17 | 3 | V03 | XX | +13, −21 | FP mos loss due to DNA degredation or amplification | XX, +13, −21, |
| | ER20 | 5 | V04 | XX | | | 46, XX |
| | ER25 | 6 | V05 | XY | mos −2, mos −9q (70-140M) | mos +9:0-15M, 15M-30M, filtered | XY, −2, −9q (low mosaic) |
| | ER26 | 7 | V07 | XX | | Risk of low level of mos −3p, not detected. | 46, XX |
| | ER27 | 8 | V08 | XY | | mos +9:0-15M, 20M-35M, filtered | 46, XY |
| | ER33 | 9 | V09 | XX | | | 46, XX |
| | ER32 | 10 | V10 | XY | | | 46, XY |
| | ER30 | 11 | V11 | XY | | | 46, XY |
| | iG-1 male mix | 12 | V12 | XY | | Reference | 46, XY |
| Run4 | ER-7 | 1 | V01 | XX | +22 | | 47 XX, +22 |
| | ER-8 | 2 | V02 | XY | | | 46 XY |
| | ER-10 | 3 | V03 | XY | +2p:0-65M | risk of mos +6:85M-100M, 6:105M-115M | 46 XY, +2p |
| | ER-12 | 4 | V04 | XX | | | 46 XX |
| | ER-15 | 5 | V05 | XX | | | 46 XX |
| | ER-28 | 6 | V07 | XX | mos +6p:10M-40M | | 48 XX, +6, +16 (low mosaic) |
| | ER-35 | 7 | V08 | XY | | | 47 XY, +21 |
| | ER-40 | 8 | V09 | XY | | | 46 XY |
| | ER-47 | 9 | V10 | XY | | | 46 XY |
| | ER-48 | 10 | V11 | XY | | | 46 XY |
| | iG-1 male | 11 | V12 | XY | | Reference | 46 XY |

Example 5—Aneuploidy Screening of Products of Conception Samples

Materials and Methods

Biospecimens 2-5 mg chronic villi tissue from product of conception (POC) were collected from miscarriage cases. Genomic DNA for sequencing was extracted using the method of Example 1. The POC specimen were also subjected to routine genetic testing for aneuploidy. The genetic testing was performed by G-banding karyotyping and FISH analysis in a clinical reference lab and were furthered confirmed by chromosomal microarray analysis (CMA) when requested. The final genetic testing results were compared with the aneuploidy testing results performed by rapid nanopore sequencing.

Nanopore Sequencing

Approximately 50 ng gDNA from each sample were subjected to the rapid direct ligation based short-read nanopore library preparation as described in Examples 2 and 3. Approximately 0.4 pmol final library were subjected to a MinION R9.4.1 RevD flowcell (Oxford Nanopore, R9.4.1 RevD). The sequencing runs were set to 3 hour run time using the LSK109 script with fast basecalling on MinIT v19.05.2 software. The sequencing results were collected in real-time for the first 2 hours.

Data Analysis

The sequencing results were collected in real-time in fastq format, and subjected to the data analysis pipeline consisting of demultiplexing, adapter cleanup, alignment, and chromosomal copy number analysis as described in Example 3. The relative copy number of chromosomes were analyzed in 10M windows when compared with a normal male reference constructive based on a census of multiple normal male samples analyzed by short-read nanopore sequencing.

Results

Aneuploidy Testing Using Rapid Nanopore Aneuploidy Testing

Figure 9:
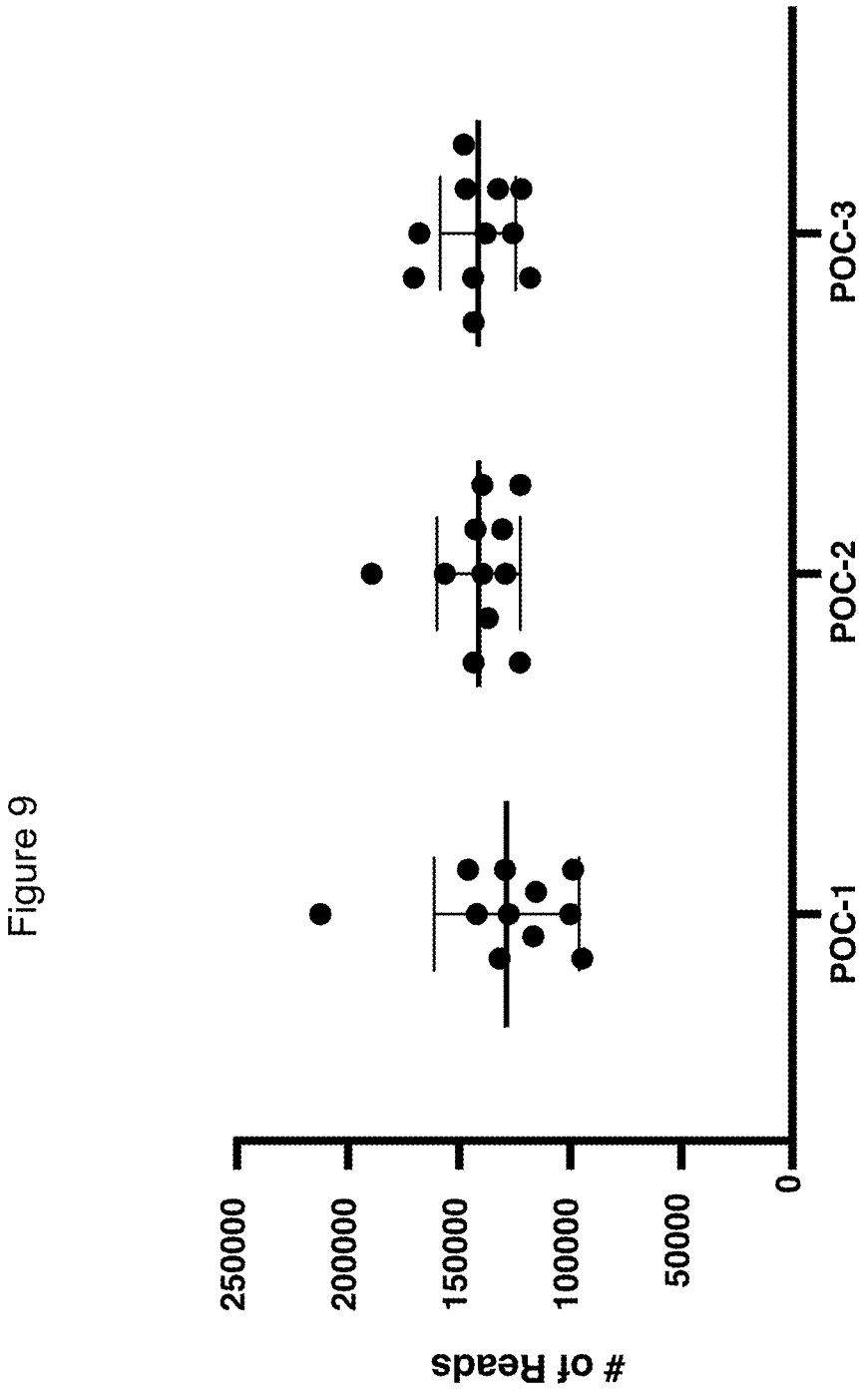
FIG. 9 shows the results of the use of rapid nanopore sequencing method for aneuploidy screening of products of conception.

In 2 hours, short-read nanopore sequencing generated 1.61-1.73M reads that passed the basecaller's quality filter. 94,718 to 212,505 reads were assigned to each sample, with a CV of barcode assignment of 11.96-25.40% (FIG. 9). The aneuploidy testing was performed using 80,000 uniquely aligned reads from each sample. Overall, the testing on POC specimen detected 16 euploid samples, and 17 aneuploidy samples at gDNA level (Table 8). Of the aneuploidy samples detected, 2 trisomy 7, 1 trisomy 9, 1 trisomy 10, 3 trisomy 16, 2 trisomy 21, 5 trisomy 22, 2 monosomy X, and one complex aneuploidy with trisomy 7 and trisomy 15 were identified (p<0.0001). Sample 2 in the POC-1 run was detected as normal female, but it failed in cell culture in the routine genetic testing and had no genetic testing result for comparison. It was excluded from the calculation of the detection sensitivity and specificity of nanopore aneuploid testing assay, but it indicated a potential benefit of the culture-independent nanopore aneuploidy testing assays. Sample 9 in the POC-2 run was detected as an euploid female. It was a tetraploid (euploid) female as tested by G-banding karyotype. It was still an euploid sample and was out of the detection limit of an aneuploidy testing. The nanopore aneuploidy screening results on 6 samples were not concordant with genetic testing results performed by G-banding and required further confirmation.

Revisiting the Discordant Samples

The nanopore aneuploidy testing results of 6 samples were not concordant with genetic testing results performed by G-banding and required revisiting the original testing results. On revisiting the G-banding karyotype for sample 7 in the POC-3 run (Table 8), it was confirmed that the G-banding result should be 47 XX, +9 instead of trisomy 8, in concordant with the nanopore testing results. On revisiting the sample 8 in the POC-3 run by rerunning FISH on the slide (Table 8), it was confirmed that this sample has at approximately 92% 47 XY, +10, in concordant with the nanopore aneuploidy screening result, instead of the original genetic testing results of a normal male. Sample 5 in the POC-1 run was detected as a complex aneuploidy with both After careful reviewing the aneuploidy screening results, the detection sensitivity of aneuploidy using nanopore aneuploidy testing assay was 17/17 (100%) and the detection specificity was 16/16 (100%) at gDNA level. It also helped to correct some misinterpreted clinical genetic testing results. Due to cost-benefit justification, POC from miscarriage were not always subjected to genetic testing. When subjected to genetic screening, they were less likely to be subjected to CMA. Nanopore aneuploidy testing can offer a cost-effective option to determine the cause of miscarriage, with same-day results.

TABLE 8

Results of POC Aneuploidy Testing

| Run | Sample | ID | Barcode | Sex | Aneuploidy | Comment | G-band | Revisit | Re-revisit by microarray |
|---|---|---|---|---|---|---|---|---|---|
| POC-1 | 1 | LL18-0026 | V12 | XY | | Reference | | | |
| | 2 | LL18-0027 | V01 | XX | | | Culture Failure-No Result | N/A | N/A |
| | 3 | LL18-0031 | V02 | XY | +22 | | 47, XY, +22 | | |
| | 4 | LL18-0032 | V03 | XY | | | 46, XY | | |
| | 5 | LL18-0034 | V04 | XX | +7, +15 | | 47, XX, +15 | | 48, XX, +7, +15 |
| | 6 | LL18-0035 | V05 | XX | +7 | | 47, XX, +7 | | |
| | 7 | LL18-0036 | V07 | XY | | | 46, XY | | |
| | 8 | LL18-0039 | V08 | XY | +22 | | 47, XY, +22 | | |
| | 9 | LL18-0044 | V09 | XX | +22 | | 47, XX, +22 | | |
| | 10 | LL18-0047 | V10 | XY | | | 46, XY | | |
| | 11 | LL19-0003 | V11 | XX | +21 | Or high level mosaic +21, noisy | 47, XX, +21 | | |
| POC-2 | 1 | LL19-0017 | V02 | XY | | Noisy | 46, XY by FISH | | |
| | 2 | LL19-0018 | V01 | XY | | | 45, X | | 46 XY |
| | 3 | LL19-0019 | V03 | XO | XO | | 45, X | | |
| | 4 | LL19-0020 | V04 | XY | | | 46, XY | | |
| | 5 | LL19-0021 | V05 | XX | | | 46, XX by FISH | | |
| | 6 | LL19-0023 | V07 | XO | XO | | 45, X | | |
| | 7 | LL19-0024 | V08 | XY | +16 | | 47, XY, +16 | | |
| | 8 | LL19-0025 | V09 | XX | +7 | | 47, XX, +7 | | |
| | 9 | LL19-0026 | V10 | XX | | | 92, XXXX | | |
| | 10 | LL19-0027 | V11 | XX | | | 46, XX | | |
| | 11 | CVS-male | V12 | XY | | Reference | | | |
| POC-3 | 1 | LL19-0038 | V02 | XY | | | 46, XY by FISH | | |
| | 2 | LL19-0039 | V03 | XX | +21 | | 47, XX, +21 | | |
| | 3 | LL19-0061 | V01 | XX | +22 | | 47, XX, +22 | | |
| | 4 | LL19-0097 | V04 | XY | +16 | | 47, XY, +16 | | |
| | 5 | LL19-0098 | V05 | XX | | | 45 XX, −21 by FISH | 97% Monosomy 21; 3% Normal | 46 XX |
| | 6 | LL19-0099 | V07 | XX | +16 | | 47, XX, +16 | | |
| | 7 | LL19-0100 | V08 | XX | +9 | | 47, XX, +8 | Re-reviewed karyotype. extra chr likely 9 and not 8. | |
| | 8 | LL19-0103 | V09 | XY | +10 | | 46, XY | Re-FISHed slide-92% 47, XY, +10 | |
| | 9 | LL19-0104 | V10 | XX | | | 46, XX | | |
| | 10 | LL19-0105 | V11 | XX | +22 | | 47, XX, +22 | | |
| | 11 | CVS-male | V12 | XY | | Reference | | | | trisomy 7 and 15 of high confidence; the genetic testing only detected trisomy 15. A genetic testing using CMA confirmed the presence of both trisomy 7 and trisomy 15. Sample 2 in the POC-2 run and sample 5 in the POC-3 were initially tested as aneuploid by genetic testing (45 XO and 45 XX, 21, respectively), but detected as normal by nanopore aneuploidy screening. A further microarray confirmation using the gDNA extracted in this study determined that these samples carried no aneuploidy. This indicated a potential false negative detection in genetic testing, a sample mislabeling, or a mosaic sample when the location of sampling can cause discrepancy in genetic testing results.

Example 6—Cancer Screening

It was first investigated if a cancer panel screening assay can be performed on a nanopore sequencer. The first challenge was that cancer panel amplicon lengths are typically greater than 320 bp (for example, Illumina TruSeq Cancer Panel hotspot v2's final amplicon products are only about 310 bp in length), and nanopore sequencing performs poorly on fragments of greater than 450 bp in length. Thus, in addition to manufacturer's 34-bp native barcoding adapters, a set of 118-bp long barcoding (LB) adapters compatible with nanopore sequencing library preparation was prepared. An amplicon was first ligated to a barcoding adapter and then to nanopore sequencing adapters using the method of Example 2 except longer barcodes were used.

To evaluate the effects of barcoding adapters, 4 Formalin-Fixed Paraffin-Embedded (FFPE) tissue samples were subjected to Illumina TruSeq Cancer Panel hotspot v2 and the 310-bp amplicons were subjected to: (1) 34-bp native barcoding adapters (ONT, EXP-NBD103); and (2) 118-bp long barcoding adapters for library preparation and nanopore sequencing. The Cancer Panel library prepared with 34-bp NB adapter generated 37,414 reads in the first 2 hours, and it was thus not possible to perform successful cancer screening assay for multiple samples within the flowcell's 48-hour sequencing life. The library prepared with the approximately 118-bp LB adapter generated 333,747 reads in the first 2 hours (Table 9). The LB adapter improved sequencing yields 9-fold. The sequencing data were used to accurately called cancer variants in the 4 lung and colorectal FFPE tissue training samples using a lung and colorectal cancer panel according to the source of tissue (Table 10). Average read coverage of each amplicon was 92-165 with one outlier that had three reads. The frequency of detected variants ranged from 13% to 58%. Sample 1 and 3 were identical samples run as technical replicates. The same variants on PICK3CA and KRAS were detected, but at different frequencies; an indication that coverage was too low to reliably determine variant frequency. Sample 4 carried a deletion mutation on the STK11 gene on Chr19:1, 207,035 covered by 3 out of 3 reads, consistent with NGS result.

TABLE 9

| Long barcodes to enable cancer profile | |
| --- | --- |
| Barcode ID | Sequence |
| 3X-B01 | CGAAGATGCGAAGAAAGTTGTCGGTGTCTTTGTGAGATGTGTATAAGAGACAG-GTTTTCGCATTTATCGTGAAACGCTTTCGCGTTTTTCGTGCGCCGCTTCAGCAG (SEQ ID NO: 13) |
| 3X-B02 | CGTTGCAGCGTCGATTCCGTTTGTAGTCGTCTGTAGATGTGTATAAGAGACAG-GTTTTCGCATTTATCGTGAAACGCTTTCGCGTTTTTCGTGCGCCGCTTCAGCAG (SEQ ID NO: 14) |
| 3X-B03 | CTGCCAGAAGGAGTCTTGTGTCCCAGTTACCAGGAGATGTGTATAAGAGACAG-GTTTTCGCATTTATCGTGAAACGCTTTCGCGTTTTTCGTGCGCCGCTTCAGCAG (SEQ ID NO: 15) |
| 3X-B04 | CCTGTTCTTGTTCGGATTCTATCGTGTTTCCCTAAGATGTGTATAAGAGACAG-GTTTTCGCATTTATCGTGAAACGCTTTCGCGTTTTTCGTGCGCCGCTTCAGCAG (SEQ ID NO: 16) |
| 3X-B05 | CGAAGGATTGCTTGTCCAGGGTTTGTGTAACCTTAGATGTGTATAAGAGACAG-GTTTTCGCATTTATCGTGAAACGCTTTCGCGTTTTTCGTGCGCCGCTTCAGCAG (SEQ ID NO: 17) |

Overall, the preliminary results indicated that sequencing data from nanopore sequencing can be used for cancer screening with the assistance of a long adapter, but that higher coverage on each amplicon is needed to perform reliable variant detection.

TABLE 10

| | | | | | Frequency | | Concordant with NGS? |
| --- | --- | --- | --- | --- | --- | --- | --- |
| Sample | Source | Gene | Location | Mutation | (%) | Coverage | (Y/N) |
| 1 | Colorectal | PICK3CA | Chr3: 178,952,085 | A > T | 17 | 92 | Y |
| 1 | Colorectal | KRAS | Chr12: 25,378,562 | C > T* | 16 | 134 | Y |
| 2 | GIST | KIT | Chr4: 55,593,613 | T > A | 38 | 111 | Y |
| 3 | Colorectal | PICK3CA | Chr3: 178,952,085 | A > T | 25 | 133 | Y |
| 3 | Colorectal | KRAS | Chr12: 25,378,562 | C > T* | 13 | 165 | Y |
| 4 | Lung | KRAS | Chr12: 25,398,285 | C > A* | 58 | 128 | Y |
| 4 | Lung | STK11 | Chr19: 1,207,035 | DelIns-TC | 100 | 3 | Y |

Summary of Cancer Screening results using Nanopore sequencing. (*Detected as reverse compliments)

To develop and validate a library for a cancer panel, first the DNA is extracted from the biological sample using the method of Example 1. This should take about 15 minutes.

Target Enrichment

Next the target enrichment protocol is done in under 30 minutes by optimizing and shortening the time needed for first round target enrichment in AmpliSeq by using a high-fidelity rapid DNA polymerase and using the amplicons directly for nanopore sequencing. NEB Q5 and KAPA High Fidelity (HiFi) DNA polymerase are the two most widely-used high-performance HiFi DNA polymerase that had been reported to produce a greater than 200-fold higher fidelity than Taq, less amplification bias and amplify at speeds of 20-30 s/kb (Potapov and Ong 2016). NEB Q5 and KAPA are systemically investigated as alternative DNA polymerases to the AmpliSeq HiFi Mix.

gDNA is subjected to AmpliSeq Cancer HotSpot Panel v2 target enrichment using: 1) AmpliSeq HiFi Mix with the manufacturer's standard PCR protocol; 2) AmpliSeq HiFi Mix with reduced extension; 3) NEB Q5® High-Fidelity DNA Polymerase; 4) NEBNext Direct Q5® Master Mix; 5) KAPA 2G Polymerase; and 6) KAPA3G DNA Polymerase. DNA yield is monitored in real-time using SyBr Green, and final products are examined on agarose gels, cleaned, and quantified using Qubit HS dsDNA assays. The enriched products are subjected to a run of MiSeq or Nanopore sequencing to determine if the alternative NEB Q5 DNA polymerase can amplify the cancer panel targets efficiently without a prolong 4-min extension. It is expected that this method will reduce the time to efficiently enrich the cancer panel targets to 30 minutes.

Library Preparation

Figure 10:
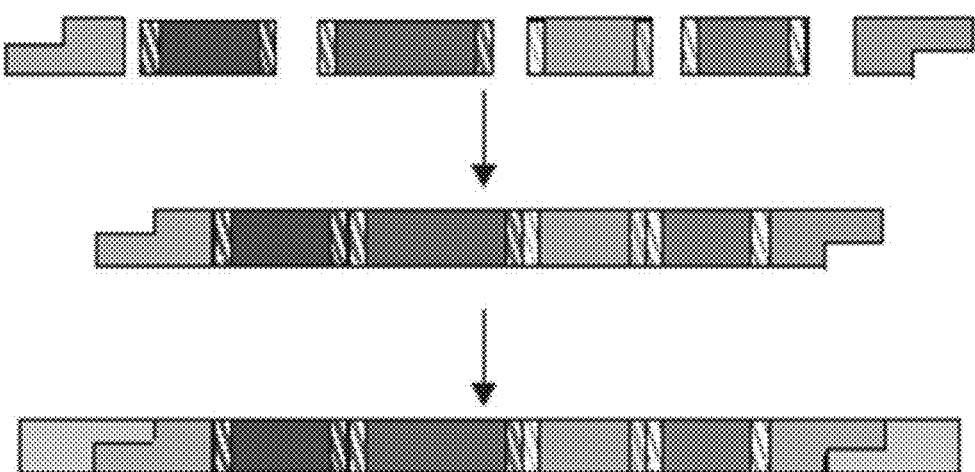
FIG. 10 is an illustration of proposed concatenation-based nanopore library preparation. Short amplicons will be concatenated by blunt-end ligation to form long fragments (≥400 bp), and then attached to a short barcoding adapter on both sides. The short-barcoded adapter is compatible with nanopore sequencing adapters and can be ligated through the 6-bp sticky ends. Components are indicated in color (Purple, dark blue, green, and red: different amplicons; blue: short barcoding adapter; orange: nanopore sequencing adapter). The primer regions of each amplicon are known as indicated by swatch.

Next to develop and validate a robust library preparation for cancer panel screening assays in 45 minutes a concatenation approach is used as illustrated in FIG. 10 as a method to simultaneously obtain reads of the necessary length and improve sequencing efficiency by devoting a greater fraction of time sequencing amplicons and a smaller fraction of time sequencing adapters. Short amplicons are end-repaired to blunt-ends and subjected to blunt-end ligation in a mixture with short barcoding adapters that carry a blunt-end and a 6-bp sticky-end. An amplicon can either concatenate to other amplicons, leading to an extension in length, or ligated to a short barcoding adapter, leading to termination of blunt-end ligation. The ligation efficiencies of blunt ends and sticky ends are both greater than 95% using the ligation condition within 10 minutes so that the final ligation product is predictable. For example, if 50-bp amplicons are mixed with 1/9 short barcoding adapter, there is a 9.5% chance it will ligate to a barcoding adapter, and 85.5% chance that it will ligate to another amplicon. The chance of the resulting concatenated library less than 450 bp is 7.22%, and the chance of it concatenate to at least 15 amplicons is less than 10%.

In Experiment 1: 50-bp, 100-bp, and 140-bp short amplicons are used to estimate the ligation products. Short amplicons are mixed with short barcoding adapters in a different ratio, subjected to in-house high efficient ligation condition, and the ligation products are examined on an agarose gel. The experiment will define the range of amplicon:barcoding adapter ratios to be used for AmpliSeq amplicons.

In Experiment 2: Amplicons from a successful $1^{st}$ round Illumina AmpliSeq Cancer Panel IHotSpot v2 target enrichment are used to determine the final amplicon:barcoding adapter ratio. Amplicons are subjected to the protocol in Example 2 and mixed with the barcoding adapter at the range of ratios as determined in Experiment 1. Then, they are subjected to the in-house highly efficient ligation condition, and the ligation products are examined on agarose gels. The ratio that ensures the majority of ligation products are 400-1000 bp, are used for library construction.

In Experiment 3: Two approaches are compared to concentrate final libraries after concatenated amplicons are ligated to nanopore sequencing adapter: 1) Rapid direct ligation of Example 2 using the ratio as determined by Experiment 2. 2) 2-step ligation: The concatenated products are first purified and size selected (greater than 400 bp) in 5 minutes, and then ligated to nanopore sequencing adapters in a highly efficient purification-free ligation condition for 10 minutes. The highly efficient purification-free ligation condition ensures greater than 95% sticky-end ligation and is directly compatible with nanopore sequencing. Final library concentration is quantified using a Qubit dsDNA HS assay kit. The approach that can efficiently generate a greater than or equal to 900 ng final library will be used for future nanopore cancer panel screening assays.

These methods are expected to result in a library preparation protocol to sequence cancer panel amplicons on a nanopore sequencer under 45 minutes, instead of the current span of days to weeks.

Sequencing

As shown in Examples 3-5, short read nanopore sequencing libraries were loaded to a sequencing flowcell to generate about 2.0 M reads in 2 hours. This was sufficient to detect aneuploidy in 5 samples within 2 hours.

In order to achieve a maximum sequencing yield, two approaches are used to increase the final library concentration: 1) Increase the concentration of the loaded library by construction a short-read nanopore sequencing library from gDNA at an excessive amount, and load 1-nmol, 2-nmol, 3-nmol, and 4-nmol to individual nanopore flowcell and compare the sequencing yield. The theoretical sequencing output is greater than 1M reads/hr when it reaches the maximum performance. It can be used to accommodate 4 samples on one flowcell, reducing the cost of the assay; and. 2) Manipulate the accessible space of the library.

Data Analysis

The sequencing results are collected in real-time in fastq format and subject to the data analysis pipeline consisting of demultiplexing, adapter cleanup, alignment, and chromosomal copy number analysis as described in Example 3.

Example 7—Rapid-Tag-Tagmentation Duplex Method

Preparation of Barcoded Tn5 Enzyme

A range of EZ-Tn5 compatible barcoded duplexes were designed based on the DNA-CS sequences. A library of DNA-CS was constructed using the nanopore rapid barcoding kit (ONT, RBK004) following manufacturer's protocol and sequenced on a MinION FLO-MIN106 flowcell. 16,734 sequences were mapped to the DNA-CS reference sequence using Geneious Assembler (V8.0.5). The consensus regions where ≥6 bp were representing 90% of the sequences were retrieved as candidates. The candidates that carried ≥8 continuous bases that were represented by at least 75% of the sequences were used as candidate barcodes. A collection of barcodes that were <50% similar to each other were used as barcodes in this study. A tagmentation duplex carried an 8-bp barcode and was compatible with the Tn5 transposase and the BAM 1D sequencing adapter. See Table 11.

TABLE 11

Barcodes for Tagmentation Protocol

| Barcode ID | Sequence | Tm (° C.) |
|---|---|---|
| S01 | CGTTGCAGCAGATGTGTATAAGAGACAG (SEQ ID NO: 18) | 59.0 |
| S02 | CGAAGGATTAGATGTGTATAAGAGACAG (SEQ ID NO: 19) | 54.6 |
| S03 | CATCATCGTAGATGTGTATAAGAGACAG (SEQ ID NO: 20) | 54.6 |
| S04 | CGAAGATGCAGATGTGTATAAGAGACAG (SEQ ID NO: 21) | 56.8 |
| S05 | CTGCCAGAAAGATGTGTATAAGAGACAG (SEQ ID NO: 22) | 56.9 |
| S06 | CGATCGTCGAGATGTGTATAAGAGACAG (SEQ ID NO: 23) | 57.9 |
| S07 | CGTTAATGCAGATGTGTATAAGAGACAG (SEQ ID NO: 24) | 55.5 |
| S08 | CTTCCGATCAGATGTGTATAAGAGACAG (SEQ ID NO: 25) | 56.3 |
| S09 | CGACGCTCTAGATGTGTATAAGAGACAG (SEQ ID NO: 26) | 57.7 |
| S10 | CCTCAAATCAGATGTGTATAAGAGACAG (SEQ ID NO: 27) | 55.0 |
| 511 | CATTGATCGAGATGTGTATAAGAGACAG (SEQ ID NO: 28) | 55.0 |
| 512 | CGATATCCGAGATGTGTATAAGAGACAG (SEQ ID NO: 29) | 56.0 |

HPLC grade top and bottom oligoes were synthesized by Integrated DNA Technologies (IDT), and dissolved in nuclease-free duplex buffer (IDT, 11-01-03-01) as 100 µM stock. The top and bottom oligoes were mixed in 1:1 ratio to make 50 µM duplex. The mixture was incubated in a heat block at 95° C. for 3 minutes, and then slowly cooled down to room temperature. The 50 µM duplexes were aliquoted to small volume and stored at −20° C. until use.

Barcoded Tn5 enzyme was prepared by assembling 1.2 µL 1 un/µL EZ-Tn5 transposase (Epicentre, TNP92110) with 0.6 µL 50 µM barcoded duplex, and incubated at 25° C. for 1 hour (Picelli et al. 2014). This reaction can be scaled up. The Barcoded Tn5 can be stored at −20° C. for a month.

Rapid-Tag Library Preparation Method

Approximately 500 ng gDNA in 50 µL volume were first sheared to 1.5 kb in a microTUBE (Covaris, 520045) on a Covaris S220 using manufacturer's setting. Each sample was processed for 20 seconds. The concentration of each sample was determined by a Qubit dsDNA HS assay kit. Depending on the actual concentration of the sheared gDNA, a 15-µL or a 25-µL tagmentation reaction can be used. In this study, 2 libraries of NA12877 gDNA were prepared using 65 ng DNA treated by 1.2 unit barcoded Tn5 in a 15-µL tagmentation reaction and 1 library of CVS gDNA was prepared using 85 ng DNA treated by 1.4 unit loaded Tn5 in a 25 µL tagmentation reaction on 0.2 ml 8-well PCR-strips.

A 15-µL tagmentation reaction system consisted of 65 ng DNA, 3.75 µL 4-fold T9 buffer (1-fold T9 buffer: 5 mM MgCl$_2$, 5 mM CaCl$_2$, 10 mM HEPES, 6.5% PEG 8000, pH 8-8.5), 1.8 µL loaded Tn5, and Zymo DNA elution buffer (or Qiagen Buffer EB) topped up to 15 µL.

A 25-µL system consisted of 85 ng DNA, 6.25 µL 4×T9 buffer, 2.1 µL barcoded Tn5, and DNA elution buffer topped up to 25 µL.

The tagmentation reactions were mixed and incubated at 55° C. for 10 minutes in a thermocycler (Bio-Rad C-1000). Each reaction was quenched by adding 0.2-fold volume 100 mM EDTA and 4-fold volume 70% Gu-HCl (MP, 105696) (e.g., 5 µL 100 mM EDTA and 100 µL 70% Gu-HCl were added to a 25-µL tagmentation reaction) and incubated at RT for 2 minutes. The quenched reaction was then mixed with 1.2-fold volume AMPure XP beads in a clean low retention 1.5 mL Eppendorf tube (e.g., 156 µL AMPure XP beads for the 130 µL quenched reaction). The mixture was incubated at RT for 5 minutes, and then pelleted on a DynaMag-2 Magnet (Invitrogen, 12321D) for 2 minutes. From each tube, the supernatant was removed and the pellet was resuspended in 40 µL 10% PEG wash (Wei et al. 2018) and combined into 1 tube. The combined beads were repelleted on DynaMag-2 Magnet and the supernatant was removed. The tube with the pelleted beads were moved to an Agencourt SPRIStand (Beckman Coulter, A29182), and washed once with 10% PEG wash, and once with freshly made 80% ethanol, and the supernatants were removed. The washed beads were spun on a minicentrifuge for 10 seconds and placed back to the Agencourt SPRIStand to dry for 2 minutes. The residual ethanol can be removed by a p10 pipette to allow faster drying. The dried beads were then resuspended in 13 µL 1/5 buffer EB (2 mM Tris-Cl, pH 8.5), incubated at RT for 3 minutes, and allowed to pellet completely in 1 minute. The supernatant was retrieved as the concentrated barcoded DNA fragments. The fragmented size was examined on a 0.8% agarose gel, and the concentration was determined by Qubit dsDNA HS assay kit. Greater than 45 ng/µL barcoded DNA were recovered in each library.

The BAM 1D was concentrated to 10-fold. 150 µL BAM 1D (ONT, EXP-NBD003) was mixed with 1.8-fold volume AMPure XP beads and washed with 10% PEG wash twice. The BAM 1D was eluted in 10 µL buffer EB, and then mixed with 5 µL ultrapure glycerol (Invitrogen, 15514011). The concentrated BAM 1D was stored at −20° C. until use.

The barcoded DNA were ligated to the 10-fold BAM 1D in purification-free ligation reaction (10.4 µL concentrated DNA, 1.6 µL 10-fold BAM 1D, 0.25 µL Blunt/TA ligation master mix, 1.44 µL enhancer mix (83.33 mM MgCl$_2$, 16.67 mM ATP)) at RT for 10 minutes. The 10-fold BAM 1D was approximately 1 µM as estimated by ligation to a 1 µM duplex of the complementary 6-bp sticky-end. The amount of BAM 1D added should be 1.2 to 1.5-fold (assuming most fragments were cut once, less than 50% fragments were cut twice by the Tn5) of the estimated copy number of barcoded DNA as estimated by DNA concentration and the total volume of barcoded DNA and 10×BAM 1D should be 12 µL. This ligation condition can ligate at least 2 pmol 6-bp complementary sticky-ends at 1:1 ratio at >95% efficiency. Adding excessive amount of BAM 1D is a waste of reagents and can cause high ratio of adapter reads.

The ligation product was ready for nanopore sequencing. The ligation product was checked on 0.8% agarose gel by loading 0.5 µL. See FIG. 11.

To enable successful short-read nanopore sequencing, the end-repair efficiency was improved from approximately 30% to approximately 80% ligation efficiency of TA ends from 75.6% to 93.2%, and 6-bp sticky ends from 94.9% to 97.2%, and tethering efficiency from approximately 50% to >95%. The workflow of a 1D barcoding library was hence simplified from an 80-min manufacturer protocol to a 45-min rapid protocol.

Rapid-Tag Sequencing

A nanopore flowcell (ONT, MIN106) was QC checked and primed according to the manufacturer's protocol. A sequencing mix was prepared by assembling 35 μL 35 μL Running Buffer FM (RBF) (ONT, EXP-NBD103), 2.5 μL Flush Tether (FLT) (ONT, EXP-NBD103), 25.5 μL Loading Beads (LB) (ONT, EXP-NBD103) and 12 μL ligation product in a low retentive 1.5 mL tube. The sequencing mix was first incubated at 33° C. for 3 minutes in a heatblock and then loaded on the nanopore flowcell following manufacturer's protocol. The sequencing ran for 2 hours on MinKNOW v1.13.1.

The sequencing mix was also tested on MinKNOW v1.15.4. Local basecaller was used to translate current signal to sequences in fastq format. The sequence run was restarted after 2 hours sequencing to maintain high sequencing yield.

This rapid protocol was applied on the current nanopore sequencing platform and generated up to 664,000 reads in 2 hours, and the resulting sequences were successfully used to perform PGS assay on up to 5 barcoded samples. It was demonstrated that nanopore sequencing can also be applied for short-reads sequencing, which makes many clinical applications possible on the ultra-portable platform. This innovation shortened the turnover time of short-read sequencing from pure DNA to sequence from 20-58 hour (Ion S5 and MiSeq) to under 3 hours.

Sequencing data from the first 2 hours were used for data analysis in this study

Rapid-Tag Data Analysis

The data analysis bioinformatics pipeline had been reported in previous studies (Wei et al. 2018; Wei and Williams 2016). Briefly, Fastq format sequences generated in the first 2 hours were first converted to fasta format and subjected cutadapt v1.14 for demultiplex based on the barcodes on FRM duplexes as reported (Wei et al. 2018; Martin 2011). The demultiplexed sequences were aligned to human reference genome Hg19 using parallel blat pBlat (http://icebert.github.io/pblat/) as reported (Wei et al. 2018; Wei and Williams 2016; Wei et al. 2018a). The uniquely aligned reads on each chromosome were summarized and normalized and used to estimate the relative copy number of each chromosome using the adjusted Z-Score method reported previously (Wei et al. 2018a; Wei and Williams 2016). The Blat aligner was computationally expensive even a parallel process was used and it can take 30-150 minutes depending on available computational resources.

Example 8—Aneuploidy Screening of CVS Samples using Rapid-Tag

Using the general methods set forth in Examples 1 and 7, nanopore-based sequencing was used for onsite PGS detection. With a 15 minute gDNA extraction from CVS tissues, 45 minute library preparation workflow and under 2 hours for 10-12 multiplexed samples, normal samples and samples with full aneuploidy were detected correctly. A single sample can be sequenced within 10 minutes and/or with 2-hour or longer sequencing run for higher resolution of chromosomal abnormality.

Materials and Methods

Sample Preparation

Genomic DNA (gDNA) was extracted from blinded, excess, villus tissues (2 mg) obtained from clinically indicated chorionic villus sampling (CVS) from ten women, as well as a known male CVS sample and from a normal male B-lymphocyte cell line (GM12877, Coriell Institute) using the method of Examples 1. For each sample, fragmented gDNA from (65-85 ng) was subjected to barcoding and library preparation following a transposase-based tagmentation protocol of Example 7. Barcoded products were subjected to 1.2-fold volume AMPure XP bead purification and 10% PEG wash as reported previously (Wei et al. 2018; Wei et al. 2018a).

Sequencing

Sequencing was performed using nanopore-based sequencing on the MinION MIN106 flowcell (Oxford Nanopore, FLO-MIN106). MinKNOW v1.13.1, local basecalling, LSK109 script, and default starting voltage were used for sequencing in this study. Sequencing data from the first 2 hours were collected and used for data analysis.

Data Analysis

Data analysis was performed using a custom analysis pipeline as described previously (Wei et al. 2018a; Wei and Williams 2016). Fastq format of sequences generated in 2 hours and that passed the basecaller quality filter were first converted to fasta format and subjected cutadapt v1.14. for demultiplexing based on the in-house barcodes as reported (Wei et al. 2018a). Demultiplexed sequences were aligned to human reference genome Hg19 using parallel blat pBlat (http://icebert.github.io/pblat/) (Wei et al. 201a8; Wei and Williams 2016). Uniquely aligned reads on each chromosome were summarized and normalized and used to estimate the relative copy number of each chromosome using the adjusted Z-Score method reported previously (Wei et al. 2018; Wei et al. 2018a). Minimap2 was also evaluated as a fast aligner in this study.

Results

Sequencing Performance

A method development, technical evaluation and then pilot study experiments were conducted. In the method development experiments, a tagmentation-based library preparation method with barcoded adapters was used using gDNA extracted from a normal male B-lymphocyte cell line (GM12877, Coriell Institute). In the technical evaluation, optimized barcoded adapters were used to with the reference genomic male gDNA. In the pilot study, gDNA extracted from eleven CVS samples was utilized. CVS samples consisted of ten blinded samples: 6 normal samples (5 normal males and one normal female); 4 samples with aneuploidy of a single chromosome (two female Trisomy 21, one male Trisomy 21, and one female Trisomy 13); and one normal male CVS sample used as a technical reference (Table 12).

Figure 12:
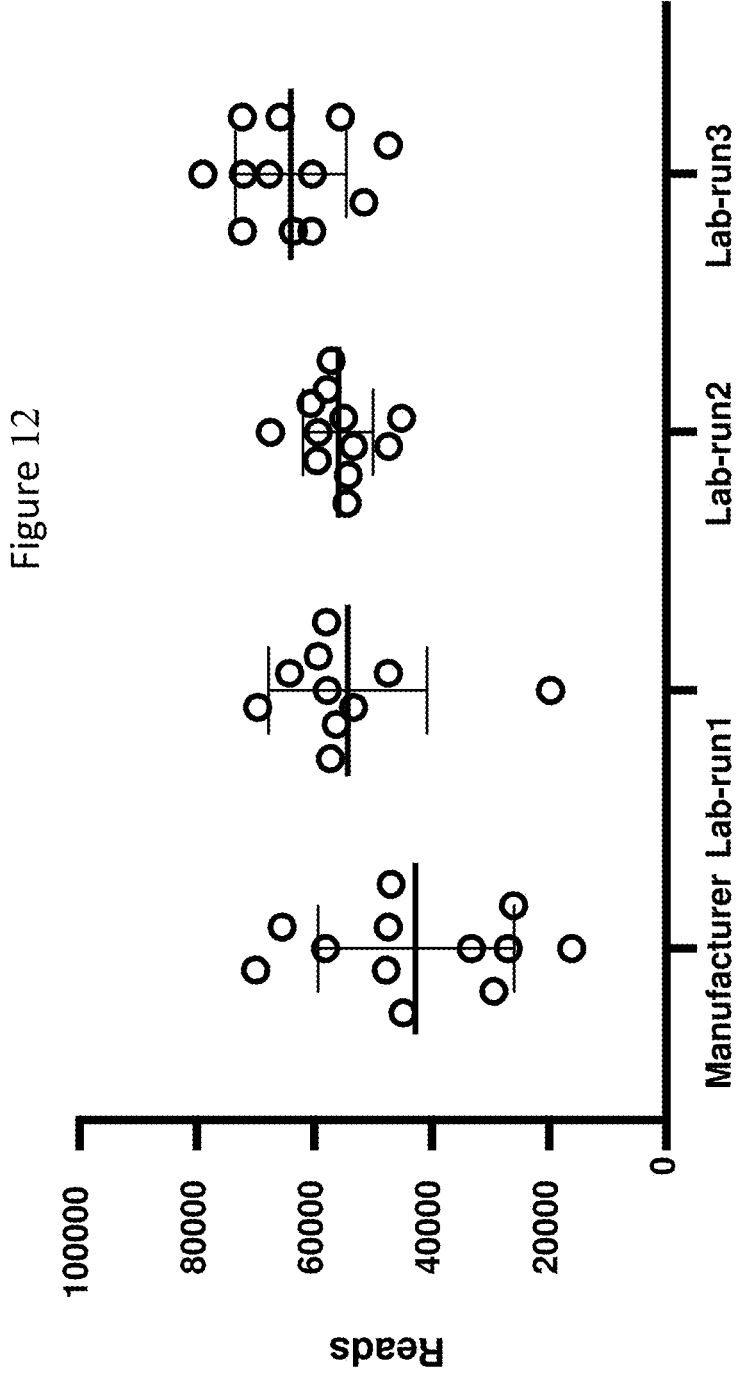
FIG. 12 is a plot showing the comparison of barcode performance using the tagmentation method. The reads assigned to each barcode are represented by a dot. The mean and SD are shown by error bars.
Figure 13:
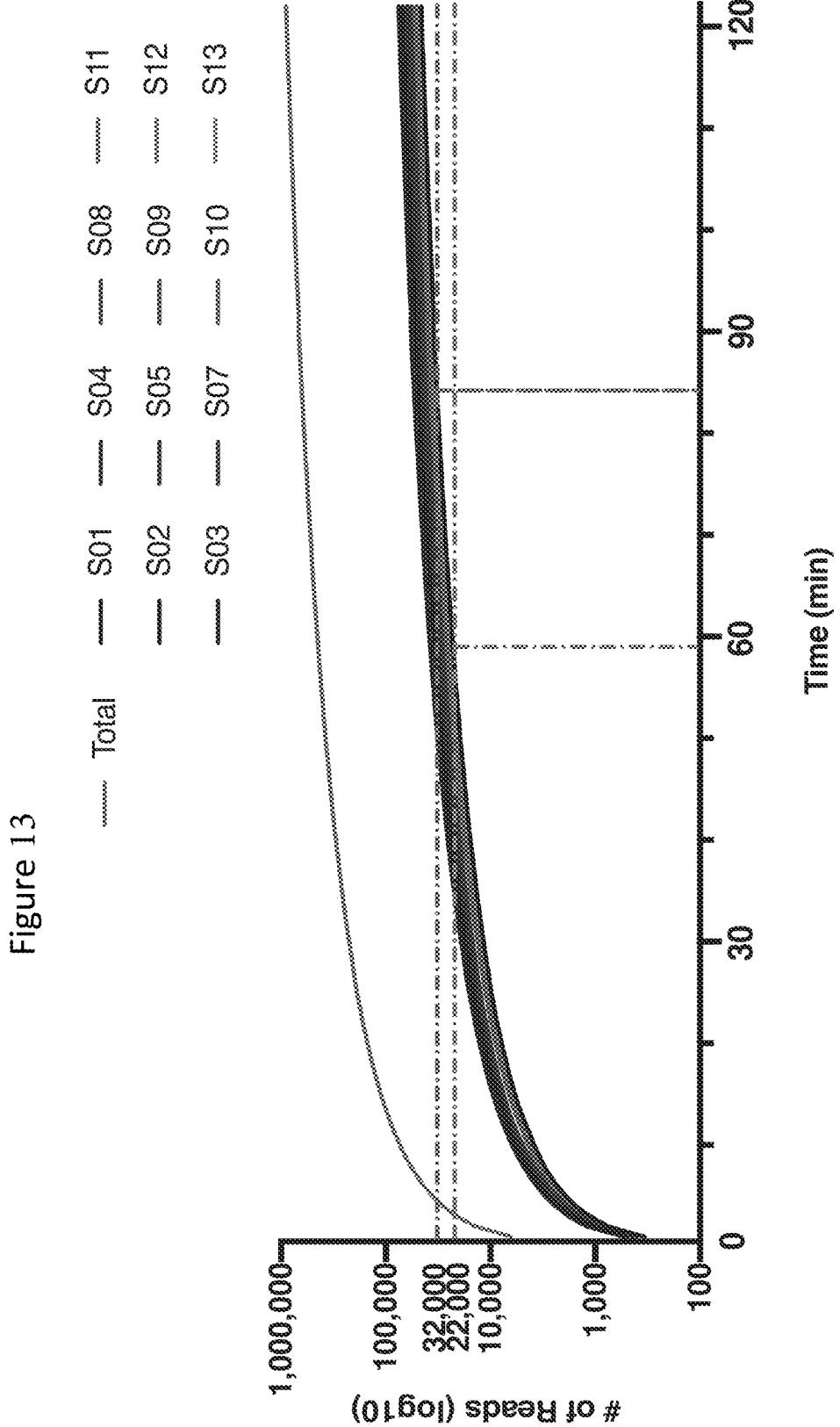
FIG. 13 shows the nanopore cumulative sequencing yield on a flowcell and for individual samples. The sequencing yield of each sample are indicated by the gray lines of different shades. The sequencing yield of the entire run is indicated by the light gray curve (top). The sequence threshold for aneuploidy detection of two confidence levels are indicated by the two dotted lines.

In the first run, transposase with 10 in-house barcodes were used to generate a sequencing library from gDNA from a normal male reference. In a 2 hour sequencing run, 725,057 reads were generated (FIGS. 12 and 13; Table 12) with 19,804-69,690 (54,349±13,498) reads assigned to each barcode. Barcode S06 was found to have generated fewer reads and a new barcode, S13, was generated and used in future runs. Of the remaining nine barcodes, 47,484 to 69,690 reads were assigned to each barcode, with a CV of 10.76% (FIG. 13; Table 13).

In the second run, twelve in-house designed barcodes were applied to prepare a library from gDNA of a normal male reference. 802,258 reads were generated in a 2-hr nanopore sequencing run. Similar to the 1st run, less than 0.1% reads were less than 50 bp in length, and 671,912 reads were suitable for analysis. Between 45,188 and 67,537 (55,993±5939) reads were assigned to each barcode. The CV of this run is 10.61%.

In the third run, gDNA from twelve samples were subjected to transposase with twelve in-house barcodes as tested in the first two runs. 930,271 reads were generated within 2-hr of nanopore sequencing. 0.1% reads were less than 50 bp in length, and 768,659 reads were used for downstream analysis. 47,447 to 79,062 (64,055±9395) reads were assigned to each barcode. Hence, all 12 samples had sufficient numbers of reads to perform aneuploidy screening within 2-hr sequencing. The CV of this run is 14.67% (FIG. 13; Table 12). The rate of sequencing runs obtained 362K-465K reads per hour through the testing. Of reads generated, greater than 75% were able to be assigned to a unique barcode. Of the assigned reads, 75-95% reads from each sample were uniquely assigned (UA) to the genome reference library (Hg19) (Table 12). Only those reads that were assigned to a barcode and uniquely matched to the reference genome library were used for subsequent downstream data analysis.

Aneuploidy Detection

Aneuploidy detection analyses requires 30,000 reads and was performed on the basis of Z-score method using the UA reads from each sample (Picelli et al. 2014).

In the tests, aneuploidy detection results using 30,000-60,000 UA sequencing reads were in agreement with results obtained using standard G-band Karyotyping for whole-chromosome aneuploidy detection (Table 13). However, aneuploidy screening can be done with 15,000 reads and sufficient numbers of reads were obtained in under 30 minutes. Normal samples/technical replicates (n=28) were detected with 0/28 false positive detection of aneuploidy using 30K UA reads (Table 13). The full trisomy cases were detected using 30K UA reads (Table 13).

TABLE 12

| Barcode performance. | | | | |
|---|---|---|---|---|
| | Manufacturer | Lab-run1 | Lab-run2 | Lab-run3 |
| Reads | 972525 | 725057 | 802258 | 930271 |
| Reads with adapters | 897595 | 544183 | 628132 | 772186 |
| Reads < 50 bp | 384501 | 690 | 751 | 1135 |
| Reads used for analysis | 513096 | 543493 | 671912 | 768659* |
| Number of barcode | 12 | 10 | 12 | 12 |
| Minimum coverage | 16195 | 19804 | 45188 | 47447 |
| Maximum coverage | 70077 | 69690 | 67537 | 79062 |
| Mean coverage of sample | 42758 | 54349 | 55993 | 64055 |
| Std. Deviation | 16695 | 13498 | 5939 | 9395 |
| Std. Error of Mean | 4819 | 4268 | 1715 | 2712 |
| Coefficient of variation (%) | 39.05 | 24.84 | 10.61 | 14.67 |

*1 samples were excluded from aneuploidy detection analysis.

TABLE 13

| Rapid-Tag run performance of aneuploidy detection. | | | | | |
|---|---|---|---|---|---|
| Run | Barcode | Reads in 2 h | MinION results | Karyotype | Concordant (Y/N) |
| 1 | S01 | 59054 | 46, XY | 46, XY | Y |
| | S02 | 53164 | 46, XY | 46, XY | Y |
| | S03 | 62300 | 46, XY | 46, XY | Y |
| | S04 | 54549 | 46, XY | 46, XY | Y |
| | S05 | 52359 | 46, XY | 46, XY | Y |
| | S06 | 17869 | 46, XY* | 46, XY | Y |
| | S07 | 51871 | 46, XY | 46, XY | Y |
| | S08 | 101676 | 46, XY | 46, XY | Y |
| | S09 | 48295 | 46, XY | 46, XY | Y |
| | S10 | 43940 | 46, XY | 46, XY | Y |
| 2 | S01 | 41214 | 46, XY | 46, XY | Y |
| | S02 | 44586 | 46, XY | 46, XY | Y |
| | S03 | 49352 | 46, XY | 46, XY | Y |
| | S04 | 38274 | 46, XY | 46, XY | Y |
| | S05 | 41383 | 46, XY | 46, XY | Y |
| | S07 | 38911 | 46, XY | 46, XY | Y |
| | S08 | 32348 | 46, XY | 46, XY | Y |
| | S09 | 39359 | 46, XY | 46, XY | Y |
| | S10 | 35698 | 46, XY | 46, XY | Y |
| | S11 | 44342 | 46, XY | 46, XY | Y |
| | S12 | 43478 | 46, XY | 46, XY | Y |
| | S13 | 41050 | 46, XY | 46, XY | Y |
| 3 | S01 | 45182 | 46, XY | 46, XY | Y |
| | S02 | 69016 | 47, XX, + 21 | 47, XX, + 21 | Y |
| | S03 | 73649 | 46, XX | 46, XX | Y |
| | S04 | 62594 | 46, XY | 46, XY | Y |
| | S05 | 57254 | Normal male reference | Normal male reference | Y |
| | S07 | 68457 | 47, XX, + 13 | 47, XX, + 13 | Y |
| | S08 | 57876 | 46, XY | 46, XY | Y |

TABLE 13-continued

| Rapid-Tag run performance of aneuploidy detection. | | | | |
|---|---|---|---|---|
| Run | Barcode | Reads in 2 h | MinION results | Karyotype | Concordant (Y/N) |
| | S09 | 52674 | 46, XY | 46, XY | Y |
| | S10 | 49684 | 47, XX, + 21 | 47, XX, + 21 | Y |
| | S11 | 61297 | 47, XY, + 21 | 47, XY, + 21 | Y |
| | S13 | 69663 | 46, XY | 46, XY | Y |

REFERENCES

Bianchi and Porter. 2014 DNA sequencing versus standard prenatal aneuploidy screening. N Engl J Med 370:799-808.

Carp, et al. 2006. Embryonic karyotype in recurrent miscarriage with parental karyotypic aberrations. Fertility and sterility 85:446-450.

Chiu, et al. 2008 Noninvasive prenatal diagnosis of fetal chromosomal aneuploidy by massively parallel genomic sequencing of DNA in maternal plasma. Proc Natl Acad Sci U S A 105:20458-63

Fragouli, et al. 2011 Cytogenetic analysis of human blastocysts with the use of FISH, CGH and aCGH: scientific data and technical evaluation. Human Reproduction 26:480-90.

Kent 2002. "BLAT—the BLAST-like alignment tool." Genome Res 12(4): 656-664.

Levy and Wapner. 2018. Prenatal diagnosis by chromosomal microarray analysis. Fertility and sterility 109:201-212.

Marr, et al. 2018. Gene silencing by RNA interference in the ectoparasitic mite, Psoroptes ovis. Vet Res 49:112.

Martin 2011 Cutadapt removes adapter sequences from high-throughput sequencing reads. EMBnetjournal. 17:10.

Miller, et al. 2003. Precise determination of mitochondrial DNA copy number in human skeletal and cardiac muscle by a PCR-based assay: lack of change of copy number with age. Nucleic acids research 31:e61.

Norton, et al. 2015 Cell-free DNA analysis for noninvasive examination of trisomy. N Engl J Med 2015;372:1589-97.

Pajnič. 2016. Extraction of DNA from Human Skeletal Material, p. 89-108. In W. Goodwin (Ed.), Forensic DNA Typing Protocols. Springer New York, New York, N.Y.

Picelli, et al. 2014 Tn5 transposase and tagmentation procedures for massively scaled sequencing projects. Genome Res. 24(12):2033-40.

Potapov and Ong 2016 Examining Sources of Error in PCR by Single-Molecule Sequencing. PlosOne 12(1):e169774.

Sahoo, et al. 2017 Comprehensive genetic analysis of pregnancy loss by chromosomal microarrays: outcomes, benefits, and challenges. Genetics in medicine: official journal of the American College of Medical Genetics. 19(1):83-89.

Tomaso, et al. 2010. Comparison of commercial DNA preparation kits for the detection of Brucellae in tissue using quantitative real-time PCR. BMC Infect Dis 10:100.

Wang and Kong 2019. "pblat: a multithread blat algorithm speeding up aligning sequences to genomes." BMC Bioinformatics 20(1): 28.

Wei, and Williams. 2016. Rapid Short-Read Sequencing and Aneuploidy Detection Using MinION Nanopore Technology. Genetics 202:37-44.

Wei, et al. 2018a. Rapid preimplantation genetic screening using a handheld, nanopore-based DNA sequencer. Fertility and sterility 110:910-916 e912.

Wei, et al. 2018b Rapid preimplantation genetic screening (PGS) using a handheld, nanopore-based, DNA sequencer. bioRxiv 2018:274563-63.

Wei, Williams, and Weiss. 2018. Rapid multiplex small DNA sequencing on the MinION nanopore sequencing platform. bioRxiv:257196-257196.

Zhang, et al. 2015. Germline Mutations in Predisposition Genes in Pediatric Cancer. N Engl J Med 373:2336-2346.

The invention claimed is:

1. A method of preparing or constructing a sequencing library for high-throughput nanopore sequencing, the method comprising:
   a. providing fragments of DNA having a size of 1000 bp or less, wherein the DNA was obtained from a sample, and wherein an amount of the DNA is less than 90 ng;
   b. incubating the DNA fragments with a Tn5 transposase and barcoded duplexes for a time and at a temperature to allow a reaction to occur;
   c. pooling and purifying Tn5-barcoded DNA fragments; and
   d. ligating the Tn5-barcoded DNA fragments to a sequencing adaptor, wherein no purification step follows the ligation step.

2. The method of claim 1, wherein the barcoded duplexes comprise a barcode region of about 8 bp.

3. The method of claim 1, wherein the barcoded duplexes comprise a nucleotide sequence chosen from the group consisting of SEQ ID NOs. 18-29.

4. The method of claim 1, wherein the sequencing adaptor has an initial concentration of 100 nM to 200 nM and is concentrated 10-fold before the ligation step.

5. The method of claim 1, wherein the amount of the DNA ranges from about 20 ng to about 90 ng.

6. The method of claim 1, wherein the amount of the DNA ranges from about 45 ng to about 85 ng.

7. The method of claim 1, wherein the amount of the DNA ranges from about 65 ng to about 85 ng.

* * * * *

SEQUENCE LISTING

<160> NUMBER OF SEQ ID NOS: 29

<210> SEQ ID NO 1
<211> LENGTH: 34
<212> TYPE: DNA
<213> ORGANISM: Artificial Sequence
<220> FEATURE:
<223> OTHER INFORMATION: synthetic barcode nucleotide

<400> SEQUENCE: 1
cgttgcagcg atgctagatg tgtataagag acag              34

<210> SEQ ID NO 2
<211> LENGTH: 34
<212> TYPE: DNA
<213> ORGANISM: Artificial Sequence
<220> FEATURE:
<223> OTHER INFORMATION: synthetic barcode nucleotide

<400> SEQUENCE: 2
cgaaggattg agcagagatg tgtataagag acag                          34

<210> SEQ ID NO 3
<211> LENGTH: 34
<212> TYPE: DNA
<213> ORGANISM: Artificial Sequence
<220> FEATURE:
<223> OTHER INFORMATION: synthetic barcode nucleotide

<400> SEQUENCE: 3
catcatcgtg tcattagatg tgtataagag acag                          34

<210> SEQ ID NO 4
<211> LENGTH: 34
<212> TYPE: DNA
<213> ORGANISM: Artificial Sequence
<220> FEATURE:
<223> OTHER INFORMATION: synthetic barcode nucleotide

<400> SEQUENCE: 4
cgaagatgcg acgttagatg tgtataagag acag                          34

<210> SEQ ID NO 5
<211> LENGTH: 34
<212> TYPE: DNA
<213> ORGANISM: Artificial Sequence
<220> FEATURE:
<223> OTHER INFORMATION: synthetic barcode nucleotide

<400> SEQUENCE: 5
ctgccagaag acctcagatg tgtataagag acag                          34

<210> SEQ ID NO 6
<211> LENGTH: 34
<212> TYPE: DNA
<213> ORGANISM: Artificial Sequence
<220> FEATURE:
<223> OTHER INFORMATION: synthetic barcode nucleotide

<400> SEQUENCE: 6
cgatcgtcgg atgaaagatg tgtataagag acag                          34

<210> SEQ ID NO 7
<211> LENGTH: 34
<212> TYPE: DNA
<213> ORGANISM: Artificial Sequence
<220> FEATURE:
<223> OTHER INFORMATION: synthetic barcode nucleotide

<400> SEQUENCE: 7
cgttaatgcg acagaagatg tgtataagag acag                          34

<210> SEQ ID NO 8
<211> LENGTH: 34
<212> TYPE: DNA
<213> ORGANISM: Artificial Sequence
<220> FEATURE:
<223> OTHER INFORMATION: synthetic barcode nucleotide

<400> SEQUENCE: 8
cttccgatcg ttaccagatg tgtataagag acag                          34

<210> SEQ ID NO 9
<211> LENGTH: 34
<212> TYPE: DNA

-continued

```
<213> ORGANISM: Artificial Sequence
<220> FEATURE:
<223> OTHER INFORMATION: synthetic barcode nucleotide

<400> SEQUENCE: 9
cgacgctctg ttcatagatg tgtataagag acag                                34

<210> SEQ ID NO 10
<211> LENGTH: 34
<212> TYPE: DNA
<213> ORGANISM: Artificial Sequence
<220> FEATURE:
<223> OTHER INFORMATION: synthetic barcode nucleotide

<400> SEQUENCE: 10
cctcaaatcg gatgtagatg tgtataagag acag                                34

<210> SEQ ID NO 11
<211> LENGTH: 34
<212> TYPE: DNA
<213> ORGANISM: Artificial Sequence
<220> FEATURE:
<223> OTHER INFORMATION: synthetic barcode nucleotide

<400> SEQUENCE: 11
cattgatcgg acgcaagatg tgtataagag acag                                34

<210> SEQ ID NO 12
<211> LENGTH: 34
<212> TYPE: DNA
<213> ORGANISM: Artificial Sequence
<220> FEATURE:
<223> OTHER INFORMATION: synthetic barcode nucleotide

<400> SEQUENCE: 12
cgatatccgg caacgagatg tgtataagag acag                                34

<210> SEQ ID NO 13
<211> LENGTH: 107
<212> TYPE: DNA
<213> ORGANISM: Artificial Sequence
<220> FEATURE:
<223> OTHER INFORMATION: synthetic barcode nucleotide

<400> SEQUENCE: 13
cgaagatgcg aagaaagttg tcggtgtctt tgtgagatgt gtataagaga caggttttcg     60
catttatcgt gaaacgcttt cgcgtttttc gtgcgccgct tcagcag                 107

<210> SEQ ID NO 14
<211> LENGTH: 107
<212> TYPE: DNA
<213> ORGANISM: Artificial Sequence
<220> FEATURE:
<223> OTHER INFORMATION: synthetic barcode nucleotide

<400> SEQUENCE: 14
cgttgcagcg tcgattccgt ttgtagtcgt ctgtagatgt gtataagaga caggttttcg     60
catttatcgt gaaacgcttt cgcgtttttc gtgcgccgct tcagcag                 107

<210> SEQ ID NO 15
<211> LENGTH: 107
<212> TYPE: DNA
<213> ORGANISM: Artificial Sequence
<220> FEATURE:
<223> OTHER INFORMATION: synthetic barcode nucleotide
```

```
<400> SEQUENCE: 15
ctgccagaag gagtcttgtg tcccagttac caggagatgt gtataagaga caggttttcg      60
catttatcgt gaaacgcttt cgcgtttttc gtgcgccgct tcagcag                  107

<210> SEQ ID NO 16
<211> LENGTH: 107
<212> TYPE: DNA
<213> ORGANISM: Artificial Sequence
<220> FEATURE:
<223> OTHER INFORMATION: synthetic barcode nucleotide

<400> SEQUENCE: 16
cctgttcttg ttcggattct atcgtgtttc cctaagatgt gtataagaga caggttttcg      60
catttatcgt gaaacgcttt cgcgtttttc gtgcgccgct tcagcag                  107

<210> SEQ ID NO 17
<211> LENGTH: 107
<212> TYPE: DNA
<213> ORGANISM: Artificial Sequence
<220> FEATURE:
<223> OTHER INFORMATION: synthetic barcode nucleotide

<400> SEQUENCE: 17
cgaaggattg cttgtccagg gtttgtgtaa ccttagatgt gtataagaga caggttttcg      60
catttatcgt gaaacgcttt cgcgtttttc gtgcgccgct tcagcag                  107

<210> SEQ ID NO 18
<211> LENGTH: 28
<212> TYPE: DNA
<213> ORGANISM: Artificial Sequence
<220> FEATURE:
<223> OTHER INFORMATION: synthetic barcode nucleotide

<400> SEQUENCE: 18
cgttgcagca gatgtgtata agagacag                                        28

<210> SEQ ID NO 19
<211> LENGTH: 28
<212> TYPE: DNA
<213> ORGANISM: Artificial Sequence
<220> FEATURE:
<223> OTHER INFORMATION: synthetic barcode nucleotide

<400> SEQUENCE: 19
cgaaggatta gatgtgtata agagacag                                        28

<210> SEQ ID NO 20
<211> LENGTH: 28
<212> TYPE: DNA
<213> ORGANISM: Artificial Sequence
<220> FEATURE:
<223> OTHER INFORMATION: synthetic barcode nucleotide

<400> SEQUENCE: 20
catcatcgta gatgtgtata agagacag                                        28

<210> SEQ ID NO 21
<211> LENGTH: 28
<212> TYPE: DNA
<213> ORGANISM: Artificial Sequence
<220> FEATURE:
<223> OTHER INFORMATION: synthetic barcode nucleotide
```

-continued

```
<400> SEQUENCE: 21
cgaagatgca gatgtgtata agagacag                                      28

<210> SEQ ID NO 22
<211> LENGTH: 28
<212> TYPE: DNA
<213> ORGANISM: Artificial Sequence
<220> FEATURE:
<223> OTHER INFORMATION: synthetic barcode nucleotide

<400> SEQUENCE: 22
ctgccagaaa gatgtgtata agagacag                                      28

<210> SEQ ID NO 23
<211> LENGTH: 28
<212> TYPE: DNA
<213> ORGANISM: Artificial Sequence
<220> FEATURE:
<223> OTHER INFORMATION: synthetic barcode nucleotide

<400> SEQUENCE: 23
cgatcgtcga gatgtgtata agagacag                                      28

<210> SEQ ID NO 24
<211> LENGTH: 28
<212> TYPE: DNA
<213> ORGANISM: Artificial Sequence
<220> FEATURE:
<223> OTHER INFORMATION: synthetic barcode nucleotide

<400> SEQUENCE: 24
cgttaatgca gatgtgtata agagacag                                      28

<210> SEQ ID NO 25
<211> LENGTH: 28
<212> TYPE: DNA
<213> ORGANISM: Artificial Sequence
<220> FEATURE:
<223> OTHER INFORMATION: synthetic barcode nucleotide

<400> SEQUENCE: 25
cttccgatca gatgtgtata agagacag                                      28

<210> SEQ ID NO 26
<211> LENGTH: 28
<212> TYPE: DNA
<213> ORGANISM: Artificial Sequence
<220> FEATURE:
<223> OTHER INFORMATION: synthetic barcode nucleotide

<400> SEQUENCE: 26
cgacgctcta gatgtgtata agagacag                                      28

<210> SEQ ID NO 27
<211> LENGTH: 28
<212> TYPE: DNA
<213> ORGANISM: Artificial Sequence
<220> FEATURE:
<223> OTHER INFORMATION: synthetic barcode nucleotide

<400> SEQUENCE: 27
cctcaaatca gatgtgtata agagacag                                      28

<210> SEQ ID NO 28
<211> LENGTH: 28
```

-continued

```
<212> TYPE: DNA
<213> ORGANISM: Artificial Sequence
<220> FEATURE:
<223> OTHER INFORMATION: synthetic barcode nucleotide

<400> SEQUENCE: 28
cattgatcga gatgtgtata agagacag                                           28

<210> SEQ ID NO 29
<211> LENGTH: 28
<212> TYPE: DNA
<213> ORGANISM: Artificial Sequence
<220> FEATURE:
<223> OTHER INFORMATION: synthetic barcode nucleotide

<400> SEQUENCE: 29
cgatatccga gatgtgtata agagacag                                           28
```